(12) United States Patent
Kondoh et al.

(10) Patent No.: US 8,135,447 B2
(45) Date of Patent: Mar. 13, 2012

(54) OPTICAL BIOLOGICAL INFORMATION MEASURING APPARATUS, OPTICAL BIOLOGICAL INFORMATION MEASURING METHOD, BIOLOGICAL INFORMATION DECISION APPARATUS, PROGRAM AND RECORDING MEDIUM

(75) Inventors: Kazuya Kondoh, Osaka (JP); Shinji Uchida, Osaka (JP)

(73) Assignee: Panasonic Electric Works Co., Ltd., Osaka (JP)

( * ) Notice: Subject to any disclaimer, the term of this patent is extended or adjusted under 35 U.S.C. 154(b) by 1459 days.

(21) Appl. No.: 10/955,862

(22) Filed: Sep. 30, 2004

(65) Prior Publication Data

US 2005/0075549 A1 Apr. 7, 2005

(30) Foreign Application Priority Data

Oct. 2, 2003 (JP) .................. 2003-344851
Oct. 2, 2003 (JP) .................. 2003-344856
Mar. 12, 2004 (JP) .................. 2004-071482

(51) Int. Cl.
*A61B 5/00* (2006.01)
(52) U.S. Cl. .................. 600/310; 345/166; 600/473
(58) Field of Classification Search .................. 600/310, 600/473; 345/166
See application file for complete search history.

(56) References Cited

U.S. PATENT DOCUMENTS

| | | | | |
|---|---|---|---|---|
| 4,295,475 A * | 10/1981 | Torzala | .................. | 600/549 |
| 5,086,229 A * | 2/1992 | Rosenthal et al. | ....... | 250/339.12 |
| 5,879,373 A | 3/1999 | Roper et al. | | |
| 6,026,313 A * | 2/2000 | Kexin | .................. | 600/310 |
| 6,101,405 A | 8/2000 | Yasuda et al. | | |
| 6,216,022 B1 * | 4/2001 | Tyrrell et al. | .................. | 600/310 |
| 6,584,340 B1 | 6/2003 | Horiuchi et al. | | |
| 2003/0158501 A1 | 8/2003 | Uchida et al. | | |
| 2004/0039287 A1 * | 2/2004 | Horiuchi et al. | .............. | 600/476 |
| 2004/0147843 A1 * | 7/2004 | Bambot et al. | ................ | 600/473 |
| 2006/0224108 A1 * | 10/2006 | Brauker et al. | ................ | 604/66 |
| 2007/0085995 A1 * | 4/2007 | Pesach et al. | .................. | 356/39 |
| 2007/0103439 A1 * | 5/2007 | Gordon et al. | ................ | 345/163 |

FOREIGN PATENT DOCUMENTS

| | | |
|---|---|---|
| CN | 1225562 A | 8/1999 |
| CN | 1358075 A | 7/2002 |
| JP | 2-172472 A | 7/1990 |
| JP | 6-319723 A | 11/1994 |
| JP | 8-215180 A | 8/1996 |
| JP | 8-238238 A | 9/1996 |

(Continued)

OTHER PUBLICATIONS

European Search Report corresponding to application No. EP 04-02-3381 dated Feb. 11, 2005.

*Primary Examiner* — Long V. Le
*Assistant Examiner* — Ellsworth Weatherby
(74) *Attorney, Agent, or Firm* — RatnerPrestia

(57) ABSTRACT

An optical biological information measuring apparatus includes a measuring surface to be placed on the surface of a living body, a mark display section which displays a mark at a region to be measured on the surface of the living body, a light-emitting section which irradiates the living body with light of a predetermined wavelength and a light-receiving section which receives light irradiated onto the living body and returned from the living body, and measures information on the living body based on the received light. The optical biological information measuring apparatus is capable of measuring biological information with improved alignment accuracy.

23 Claims, 23 Drawing Sheets

FOREIGN PATENT DOCUMENTS

| | | |
|---|---|---|
| JP | 11-56789 A | 3/1999 |
| JP | 11-239573 | 9/1999 |
| JP | 2000-155091 | 6/2000 |
| JP | 2001-37741 A | 2/2001 |
| JP | 2001-244891 A | 9/2001 |
| JP | 2002-350322 A | 12/2002 |
| JP | 2002-361923 A | 12/2002 |
| JP | 2003-310575 | 11/2003 |
| JP | 2004-288362 | 11/2009 |
| JP | 2004-288362 | 2/2010 |
| WO | WO 98/02087 | 1/1998 |
| WO | WO 00/78209 A2 | 12/2000 |

* cited by examiner

TOP VIEW

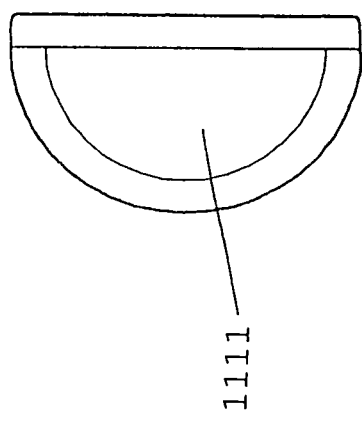
Fig.10(a)
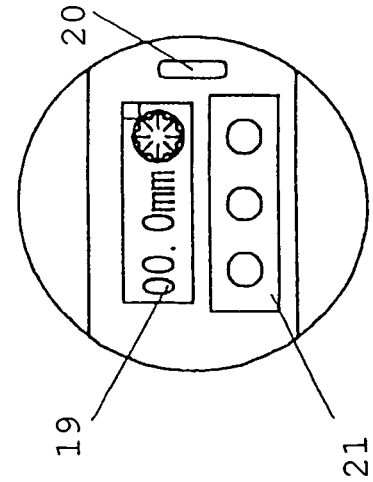
Fig.10(b) TOP VIEW
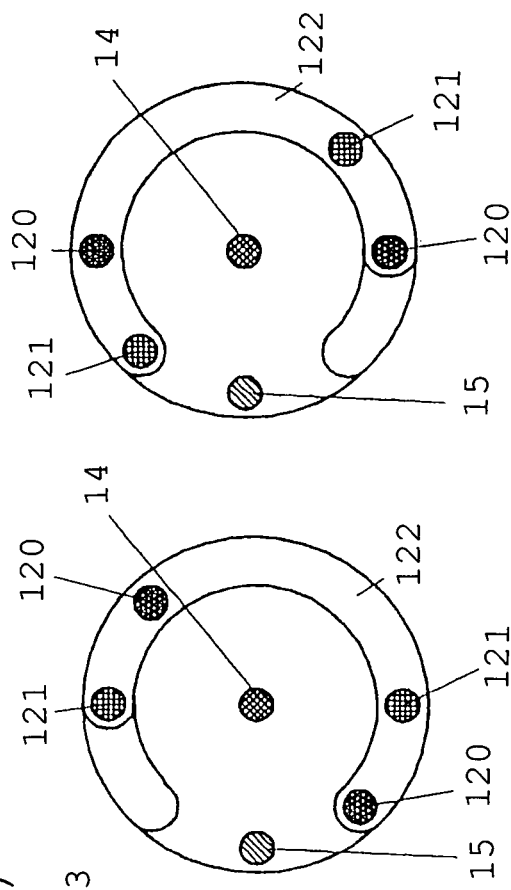
Fig.10(c)
Fig.10(d) WHEN MARK CREATION SECTION IS AT PREDETERMINED POSITION
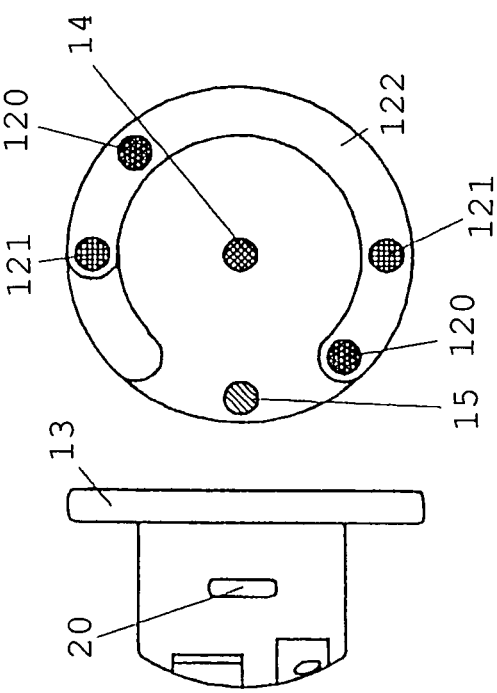
Fig.10(e) WHEN ALIGNMENT SECTION IS AT PREDETERMINED POSITION

WHEN ALIGNMENT SECTION IS AT PREDETERMINED POSITION

WHEN MARK CREATION SECTION IS AT PREDETERMINED POSITION

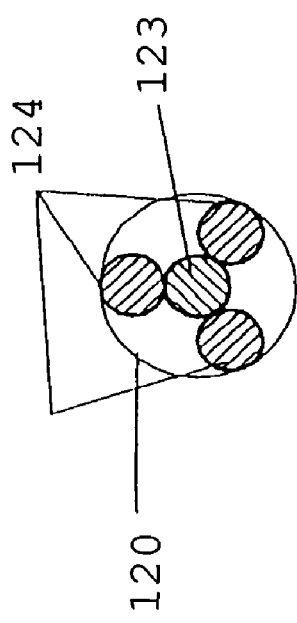
Fig.13(a)
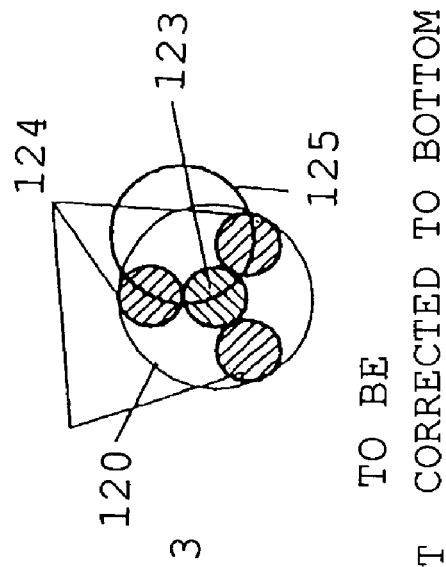
Fig.13(d) TO BE CORRECTED TO BOTTOM LEFT
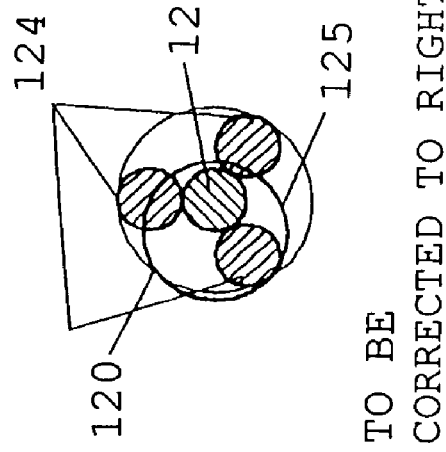
Fig.13(c) TO BE CORRECTED TO RIGHT
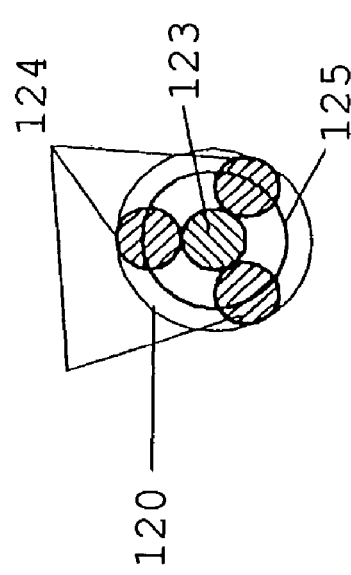
Fig.13(b) ALIGNMENT OK

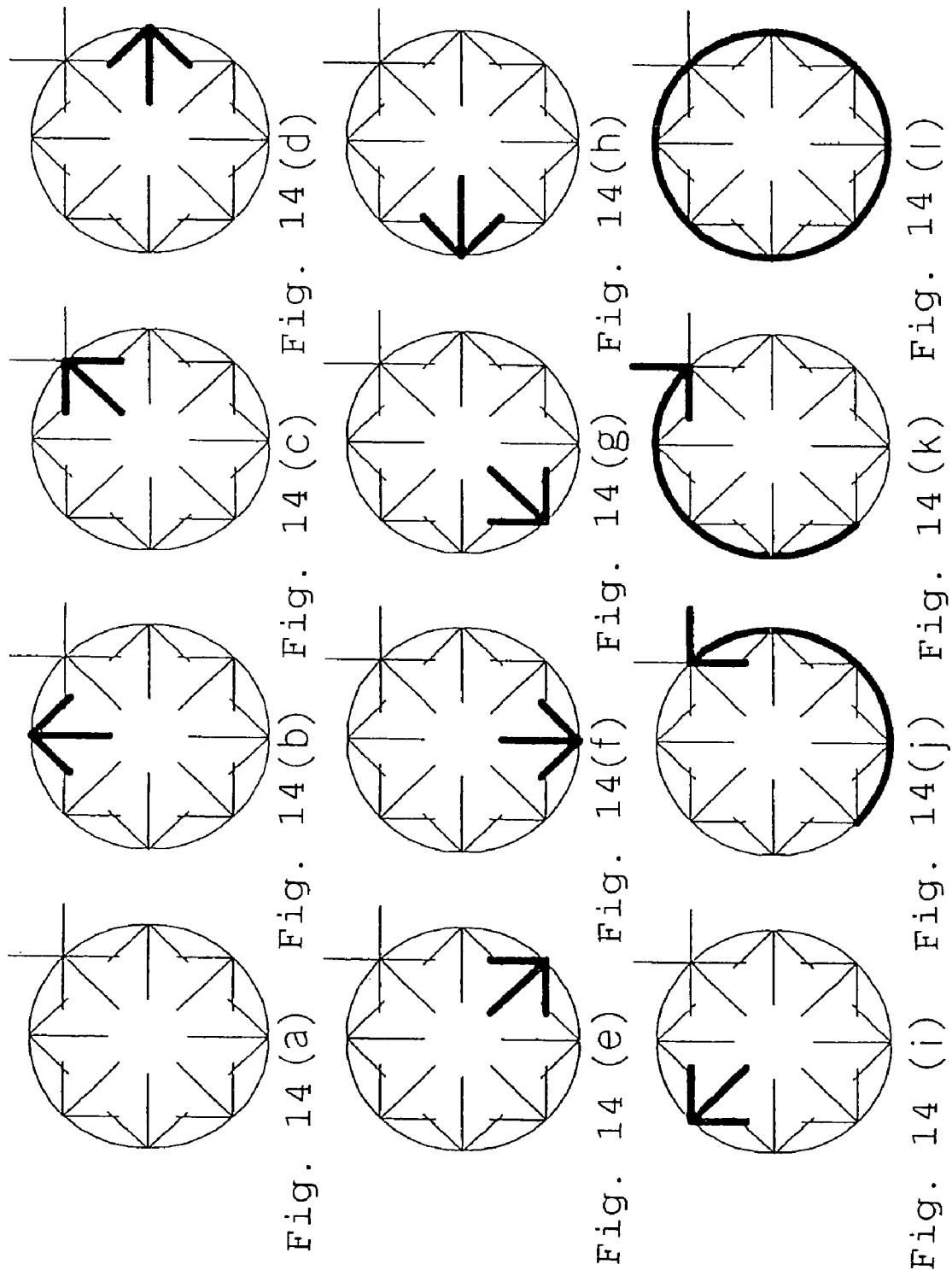

OPTICAL BIOLOGICAL INFORMATION MEASURING APPARATUS, OPTICAL BIOLOGICAL INFORMATION MEASURING METHOD, BIOLOGICAL INFORMATION DECISION APPARATUS, PROGRAM AND RECORDING MEDIUM

BACKGROUND OF THE INVENTION

1. Field of the Invention

The present invention relates to an optical biological information measuring apparatus which measures biological information using light, optical biological information measuring method, biological information decision method, program thereof and recording medium. The invention relates to, for example, an optical fat thickness measuring apparatus which measures a thickness of local panniculus and a tissue oxygen concentration measuring apparatus which measures tissue oxygen concentration of muscle.

2. Related Art of the Invention

As a conventional optical biological information measuring apparatus which measures biological information such as a thickness of local fat, there has been one that has a light-emitting section and a light-receiving section arranged on the surface of a living body and measures the thickness of fat from diffused/reflected light (for example, see Japanese Patent Laid-Open No. 11-239573 (e.g., FIG. 6)).

FIG. 20 is a block diagram of a conventional panniculus thickness measuring apparatus (e.g., see Japanese Patent Laid-Open No. 11-239573 (e.g., FIG. 6)). A light-emitting element 3 is driven by a driving circuit 2 through a command from a CPU 1 to emit near-infrared light. This near-infrared light passes through panniculus 4, is diffused/absorbed, and the reflected light thereof is received by light-receiving elements 5, 6, 7. The CPU 1 decides which output of the light-receiving elements 5, 6, 7 should be applied according to a measuring region selected by a button at a measuring region selection input section 10 and operates an analog switch 8. Then, one light-receiving input is selected by the analog switch 8 and captured by the CPU 1 through an AMP 9. Then, the CPU 1 performs calculations based on the light-receiving input and displays the measuring result on a measured value display section 50.

Furthermore, in another conventional technique, a light-emitting section and a light-receiving section have been arranged so as to obtain a plurality of different optical path lengths and variations have been corrected in skin color, etc., from a plurality of amounts of light received corresponding to the different optical path lengths obtained by the light-receiving elements (e.g., see Japanese Patent Laid-Open No. 2000-155091 (e.g., FIG. 4)).

Furthermore, there has been a further conventional technique that measures a force with which a measuring probe is pushed against a living body, adopts a protruding shape for the measuring probe to thereby correct variations in the fat thickness, stabilize the fat thickness and improve measuring repeatability (e.g., see Japanese Patent Laid-Open No. 2003-310575).

However, because the measuring surface which contacts a living body is flat in the panniculus thickness measuring apparatus having a conventional structure, it is not easy for the user to find out where a measuring region to be measured should be contacted with in the measuring surface. Furthermore, since light emitted from the light-emitting element is infrared which is invisible to human eyes, it has been impossible for the user to know whether the region to be measured has been actually measured or not. Furthermore, since it is difficult to align the measuring region, measuring positions differ from one measurement to another, thus degrading measuring repeatability. Furthermore, since the thickness of panniculus of a living body is not uniform, simple displacement in every measurement would result in a large measuring error. When measuring the effects of exercise or esthetic treatment, a large measuring error caused by displacement would result in a serious problem in checking the effects, and so it has been always necessary to measure the effects at the same position.

Furthermore, when a user of a panniculus thickness measuring apparatus having a conventional structure measures regions such as the upper arm, back of the thigh or back whose panniculus is a matter of concern, measuring regions are not easily visible to the measurer, and for this reason the measuring repeatability deteriorates due to displacement in every measurement, thus making self-measurement impossible. Since the thickness of panniculus of the back of the upper arm is not uniform, if the measuring position changes in every measurement, simple displacement would amount to a large measuring error.

The present invention has been implemented in view of the above described conventional problems and it is an object of the present invention to provide an optical biological information measuring apparatus, optical biological information measuring method, program thereof, recording medium and biological information decision apparatus using them capable of measuring biological information with high alignment accuracy.

SUMMARY OF THE INVENTION

The $1^{st}$ aspect of the present invention is an optical biological information measuring apparatus comprising:
a measuring surface to be placed on a surface of a living body;
a mark display section which displays a mark in a region to be measured on the surface of the living body;
a light-emitting section which irradiates said surface of the living body with light of a predetermined wavelength; and
a light-receiving section which receives the light irradiated onto said surface of the living body and returned from said living body.

The 2nd aspect of the present invention is the optical biological information measuring apparatus according to the $1^{st}$ aspect of the present invention, wherein said mark display section comprises a visible light source which irradiates visible light for illuminating said region to be measured.

The $3^{rd}$ aspect of the present invention is the optical biological information measuring apparatus according to the $2^{nd}$ aspect of the present invention, wherein said visible light source is placed at an end of said measuring surface.

The $4^{th}$ aspect of the present invention is the optical biological information measuring apparatus according to the $2^{nd}$ aspect of the present invention, further comprising a contact detection section which detects that said measuring surface has contacted the surface of said living body, wherein after said contact detection section detects that said measuring surface has contacted the surface of said living body, irradiation of visible light from said visible light source is stopped.

The $5^{th}$ aspect of the present invention is the optical biological information measuring apparatus according to the $4^{th}$ aspect of the present invention, wherein said contact detection section decides that said measuring surface has contacted the surface of said living body based on a variation in an amount of light received by said light-receiving section and/or by detecting attachment between said measuring surface and said living body.

The 6th aspect of the present invention is the optical biological information measuring apparatus according to the 2nd aspect of the present invention, wherein the color of said visible light irradiated by said visible light source is red.

The 7th aspect of the present invention is the optical biological information measuring apparatus according to the 1st aspect of the present invention, wherein part of the surface of said measuring surface reflects part or the whole of the visible light.

The 8th aspect of the present invention is the optical biological information measuring apparatus according to the 7th aspect of the present invention, wherein said measuring surface provides a mirrored surface.

The 9th aspect of the present invention is the optical biological information measuring apparatus according to the 1st aspect of the present invention, further comprising a calculation section which calculates the thickness of local fat based on an amount of said light which has propagated through said living body received by said light-receiving section.

The 10th aspect of the present invention is the optical biological information measuring apparatus according to the 9th aspect of the present invention, wherein said light-receiving section comprises two light-receiving elements arranged at different distances from said light-emitting section for receiving said light, and said calculation section calculates said thickness of local fat from the ratio of two amounts of light received by said two light-receiving elements based on the following expression:

$$T = A \cdot X1/X2 + B$$

(A, B denote coefficients, X1, X2 denote amounts of light received by first and second light-receiving elements)

The 11th aspect of the present invention is the optical biological information measuring apparatus according to the 1st aspect of the present invention, wherein said light-emitting section can emit light of two types of wavelength, said light-receiving section can receive said light of two types of wavelength, and said optical biological information measuring apparatus further comprises a calculation section which calculates local tissue oxygen concentration from the ratio of the respective amounts of light having said two types of wavelengths received by said light-receiving section.

The 12th aspect of the present invention is the optical biological information measuring apparatus according to the 11th aspect of the present invention, wherein said light of two types of wavelength is light having a wavelength including substantially 650 nm and light having a wavelength including substantially 850 nm.

The 13th aspect of the present invention is the biological information measuring apparatus according to the 2nd aspect of the present invention, wherein said light-receiving section can receive visible light output from said visible light source and light having said predetermined wavelength, and said biological information measuring apparatus further comprises a calculation section which calculates local tissue oxygen concentration from the ratio of amounts of said visible light received by said light-receiving section and light having said predetermined wavelength.

The 14th aspect of the present invention is a program for causing a computer to function as a calculation section which calculates said thickness of local fat based on an amount of light received by said light-receiving section of the optical biological information measuring apparatus according to the 10th aspect of the present invention.

The 15th aspect of the present invention is a computer-processable recording medium which stores the program according to the 14th aspect of the present invention.

The 16th aspect of the present invention is the optical biological information measuring apparatus according to the 1st aspect of the present invention, wherein said mark display section is a mark creation section which forms a mark at a predetermined position on said surface of the living body, and said mark creation section comprises one or more through holes formed on said measuring surface.

The 17th aspect of the present invention is the optical biological information measuring apparatus according to the 16th aspect of the present invention, wherein said through hole is placed at a position at which said light-receiving section receives no influence from outside light through said through hole.

The 18th aspect of the present invention is the optical biological information measuring apparatus according to the 1st aspect of the present invention, wherein said mark display section is a mark creation section which forms a mark at the position to be measured on said surface of the living body, an alignment section which aligns said measuring surface with the position to be measured of said surface of the living body is formed on said measuring surface, said alignment section comprises an alignment light source which irradiates light onto the surface of the living body on which said mark is formed and at least one alignment light-receiving section which receives light irradiated from said alignment light source onto said surface of the living body and receives light reflected from said surface of the living body, the absorption factor or reflection factor of the light of said mark is different from the absorption factor or reflection factor of the light in the area of said surface of the living body in which said mark is not formed, and the state of alignment of said measuring surface with said mark is decided based on light-receiving intensity at said alignment light-receiving section.

The 19th aspect of the present invention is the optical biological information measuring apparatus according to the 18th aspect of the present invention, further comprising a driving mechanism which can move the position of said alignment section to the position of the mark which said mark creation section created on said surface of the living body.

The 20th aspect of the present invention is the optical biological information measuring apparatus according to the 18th aspect of the present invention, wherein at least two of said alignment sections and said mark creation sections are formed on said measuring surface, respectively.

The 21st aspect of the present invention is the optical biological information measuring apparatus according to the 18th aspect of the present invention, further comprising a calculation section which decides an alignment status based on the light-receiving intensity at said alignment light-receiving section, wherein said alignment light source is placed in the center of said alignment section, said alignment light-receiving section comprises a plurality of light-receiving bodies arranged at uniform intervals around said alignment light source, and said calculation section decides an alignment status when intensities of light received by said respective light-receiving bodies are substantially equal and decides a non-alignment status when intensities of light received by said respective light-receiving bodies are substantially different from one another.

The 22$^{nd}$ aspect of the present invention is the optical biological information measuring apparatus according to the 21$^{st}$ aspect of the present invention, further comprising a display section which displays said alignment status or said non-alignment status, wherein said calculation section causes said display section to display the direction in which said alignment status should be set when said calculation section decides said non-alignment status.

The 23$^{rd}$ aspect of the present invention is an optical biological information measuring method of measuring information on a living body based on received light, comprising:

a step of displaying a mark at a predetermined position on a surface of the living body;

a step of aligning a measuring surface with the mark displayed on said surface of the living body;

a step of irradiating said surface of the living body with light having a predetermined wavelength; and a step of receiving light irradiated onto said surface of the living body and returned from the living body.

The 24$^{th}$ aspect of the present invention is a program for causing a computer to function as a calculation section which decides an alignment status of the optical biological information measuring apparatus according to the 21$^{st}$ aspect of the present invention based on light-receiving intensity at said alignment light-receiving section.

The 25$^{th}$ aspect of the present invention is a computer-processable recording medium which stores the program according to the 24$^{th}$ aspect of the present invention.

The 26$^{th}$ aspect of the present invention is a biological information decision apparatus comprising:

the optical biological information measuring apparatus according to the 1$^{st}$ aspect of the present invention;

an input section which inputs information on said living body;

a calculation section which performs calculations based on information input from said input section and information output from said optical biological information measuring apparatus;

a storage section which prestores biological information corresponding to the information input to said input section; and a comparison section which compares biological information prestored in said storage section and the result of the calculation performed by said calculation section, wherein said biological information decision apparatus decides the information measured by said biological information measuring apparatus.

The 27th aspect of the present invention is the optical biological information measuring apparatus according to the 1$^{st}$ aspect of the present invention, wherein said light irradiated from said light-emitting section is near-infrared light.

The 28$^{th}$ aspect of the present invention is the optical biological information measuring apparatus according to the 27$^{th}$ aspect of the present invention, wherein at least part of said measuring surface absorbs near-infrared light irradiated from said light-emitting section.

The 29th aspect of the present invention is the optical biological information measuring apparatus according to the 7th aspect of the present invention, wherein said measuring surface is convex-shaped.

The 30$^{th}$ aspect of the present invention is the optical biological information measuring method according to the 23$^{rd}$ aspect of the present invention, wherein the step of aligning the measuring surface with the mark displayed on said surface of the living body comprises a step of aligning the measuring surface which reflects part or the whole of visible light while watching said surface of the living body reflected on said measuring surface.

The present invention can provide an optical biological information measuring apparatus, optical biological information measuring method, program thereof, recording medium and biological information decision apparatus using them capable of measuring biological information with high alignment accuracy.

In the present invention, the light-emitting section irradiates infrared light. Here, the light irradiated by the light-emitting section is preferably near-infrared light. In the present specification, the infrared light refers to light having a wavelength of 700 nm or more and the near-infrared light refers to light having a wavelength ranging from 700 nm to 2000 nm.

BRIEF DESCRIPTION OF THE DRAWINGS

FIG. 7($b$) is a plan view of the optical biological information measuring apparatus according to Embodiment 3 of the present invention.

FIG. 7($c$) is a side view of the optical biological information measuring apparatus according to Embodiment 3 of the present invention.

FIG. 7($d$) is a rear view of the optical biological information measuring apparatus according to Embodiment 3 of the present invention.

FIG. 8($b$) is a perspective view of the optical biological information measuring apparatus according to embodiment 3 of the present invention.

FIG. 10($a$) is an overall view of an optical biological information measuring apparatus according to Embodiment 4 of the present invention.

FIG. 10($b$) is a plan view of the optical biological information measuring apparatus according to Embodiment 4 of the present invention.

FIG. 10(c) is a side view of the optical biological information measuring apparatus according to Embodiment 4 of the present invention.

FIG. 10(d) is a rear view of the optical biological information measuring apparatus according to Embodiment 4 of the present invention.

FIG. 10(e) is a rear view of the optical biological information measuring apparatus according to Embodiment 4 of the present invention.

FIG. 13(a) is a schematic diagram illustrating alignment using the optical biological information measuring apparatus according to Embodiment 4 of the present invention.

FIG. 13(b) is a schematic diagram illustrating alignment using the optical biological information measuring apparatus according to Embodiment 4 of the present invention.

FIG. 13(c) is a schematic diagram illustrating alignment using the optical biological information measuring apparatus according to Embodiment 4 of the present invention.

FIG. 13(d) is a schematic diagram illustrating alignment using the optical biological information measuring apparatus according to Embodiment 4 of the present invention.

FIG. 14(a) is an indicator chart indicating an alignment status or non-alignment status using the optical biological information measuring apparatus according to Embodiment 4 of the present invention.

FIG. 14(b) is an indicator chart indicating an alignment status or non-alignment status using the optical biological information measuring apparatus according to Embodiment 4 of the present invention.

FIG. 14(c) is an indicator chart indicating an alignment status or non-alignment status using the optical biological information measuring apparatus according to Embodiment 4 of the present invention.

FIG. 14(d) is an indicator chart indicating an alignment status or non-alignment status using the optical biological information measuring apparatus according to Embodiment 4 of the present invention.

FIG. 14(e) is an indicator chart indicating an alignment status or non-alignment status using the optical biological information measuring apparatus according to Embodiment 4 of the present invention.

FIG. 14(f) is an indicator chart indicating an alignment status or non-alignment status using the optical biological information measuring apparatus according to Embodiment 4 of the present invention.

FIG. 14(g) is an indicator chart indicating an alignment status or non-alignment status using the optical biological information measuring apparatus according to Embodiment 4 of the present invention.

FIG. 14(h) is an indicator chart indicating an alignment status or non-alignment status using the optical biological information measuring apparatus according to Embodiment 4 of the present invention.

FIG. 14(i) is an indicator chart indicating an alignment status or non-alignment status using the optical biological information measuring apparatus according to Embodiment 4 of the present invention.

FIG. 14(j) is an indicator chart indicating an alignment status or non-alignment status using the optical biological information measuring apparatus according to Embodiment 4 of the present invention.

FIG. 14(k) is an indicator chart indicating an alignment status or non-alignment status using the optical biological information measuring apparatus according to Embodiment 4 of the present invention.

FIG. 14(l) is an indicator chart indicating an alignment status or non-alignment status using the optical biological information measuring apparatus according to Embodiment 4 of the present invention.

DESCRIPTION OF SYMBOLS

Figure 1:
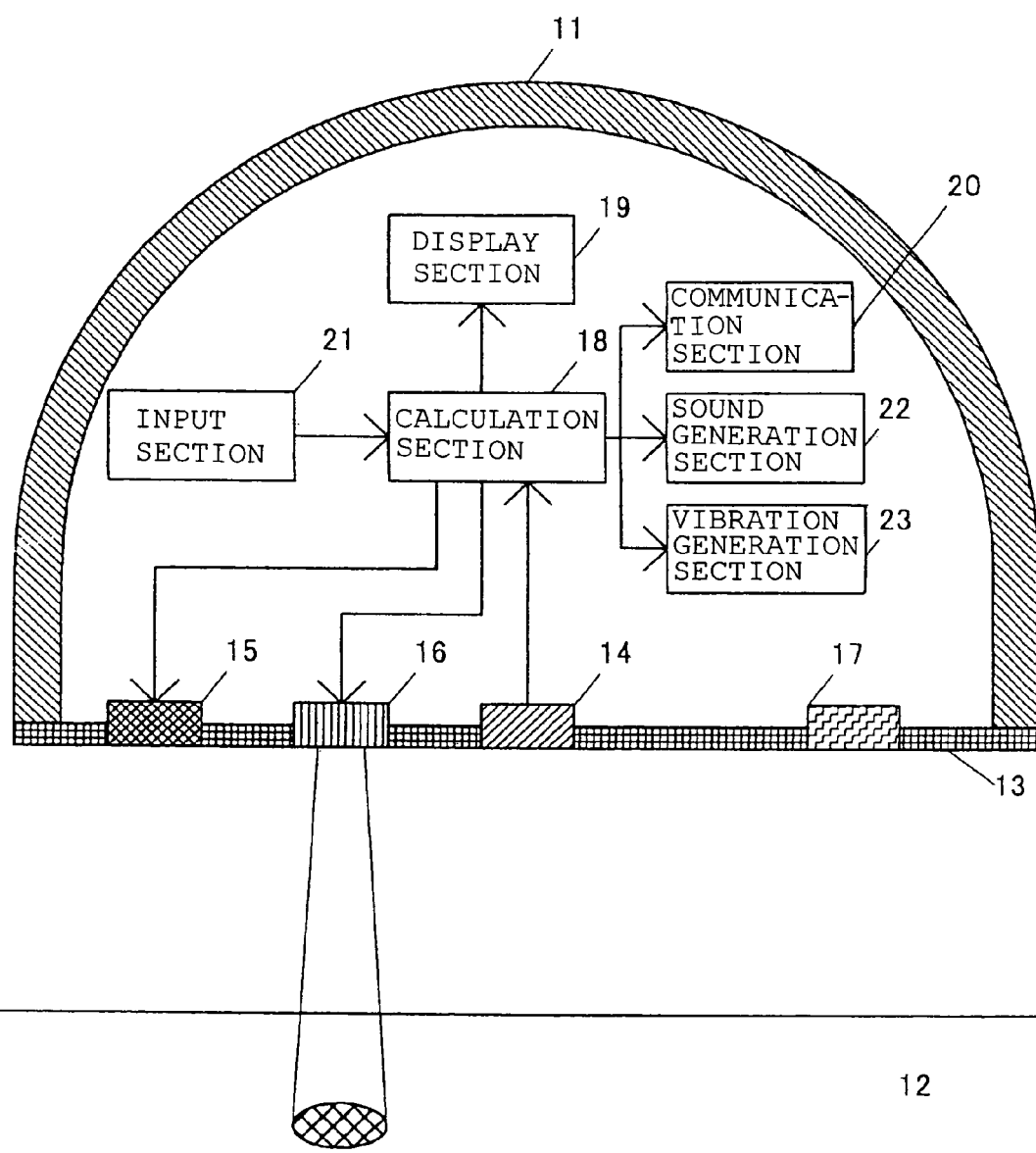
FIG. 1 is a block diagram of an optical biological information measuring apparatus according to Embodiment 1 of the present invention.

1 CPU
2 Driving circuit
3 Light-emitting element
4 Panniculus
5, 6, 7 Light-receiving element
8 Analog switch
9 AMP
10 Measuring region selective input section
11, 31, 35, 41 Optical fat thickness gauge
12 Living body
13, 33 Measuring surface
14 Light-receiving section
15 Light-emitting section
16, 36 Visible light source
17 Attachment detection section
18 Calculation section
19 Display section
20 Communication section
21 Input section
22 Sound generation section
23 Vibration generation section
24 First light-receiving element
25 Second light-receiving element

PREFERRED EMBODIMENTS OF THE INVENTION

With reference now to the attached drawings, embodiments of the present invention will be explained below.

Embodiment 1

FIG. 1 is a block diagram of an optical fat thickness gauge 11 which is an optical biological information measuring apparatus according to Embodiment 1 of the present invention.

A measuring surface 13 contacting a living body 12 is a disk-shaped flat surface having a diameter of approximately 100 mm and provides a mirrored surface. A light-receiving section 14 having a photodiode which is an optical sensor is disposed near the center. A light-emitting section 15 having an LED which emits near-infrared light including a wavelength of substantially 850 nm is disposed at a distance of approximately 45 mm from the light-receiving section 14. A preferable distance between the light-emitting section 15 and light-receiving section 14 is approximately 35 to 50 mm for measurement of the thickness of panniculus.

Here, using light having a central wavelength close to 800 to 900 nm for the light-emitting section 15 is preferable because the light-emitting section 15 is less affected by fluctuations of an absorption factor due to variations in oxidized/reduced hemoglobin and oxidized/reduced myoglobin, and measuring repeatability improves.

A visible light source 16 which is an example of the visible light source of the present invention and has a red LED is disposed almost in the center between the light-emitting section 15 and light-receiving section 14. The visible light source 16 emitting red light is preferable because the skin color does not look unhealthy.

Furthermore, an attachment detection section 17 which detects whether the measuring surface 13 is appressed to the living body or not is also disposed on the measuring surface 13. Methods of detecting attachment at the attachment detection section 17 include a method of measuring impedance of the living body 12 using electrodes, a method of detecting a pressure according to attachment and a method of measuring reflected light of the living body using a light-emitting element and light-receiving element arranged close to each other, etc. Attachment can also be detected when the amount of light received by the light-receiving section 14 falls below a specified value. In this case, the number of parts can be reduced compared to other methods Furthermore, attachment can also be detected both by the attachment detection section 17 detecting attachment and by the light-receiving section 14 detecting a variation in the amount of light received.

These attachment detection section 17 and light-receiving section 14 constitute a contact detection section of the present invention as an example.

The calculation section 18 calculates local biological information such as a thickness of panniculus from a signal obtained from the light-receiving section 14. The calculation section 18 displays the local biological information obtained on a display section 19 or sends the signal to an external device through a communication section 20.

An input section 21 can input information on the sex, age and measuring region. The calculation section 18 can also calculate information on the health condition such as an obesity index of the living body from the information input and local biological information and display the information on the display section 19. Furthermore, the calculation section 18 can also send information on the sex, age and measuring region and information on the health condition to an external device through the communication section 20. Or adversely, it is also possible to acquire information on the sex, age and measuring region from the external device through the communication section 20.

Next, the operation of measuring the thickness of local fat using the optical biological information measuring apparatus of this Embodiment 1 will be explained.

The user performs alignment while observing the position of the measuring region of the living body 12 illuminated with visible light emitted from the visible light source 16.

Figure 2:
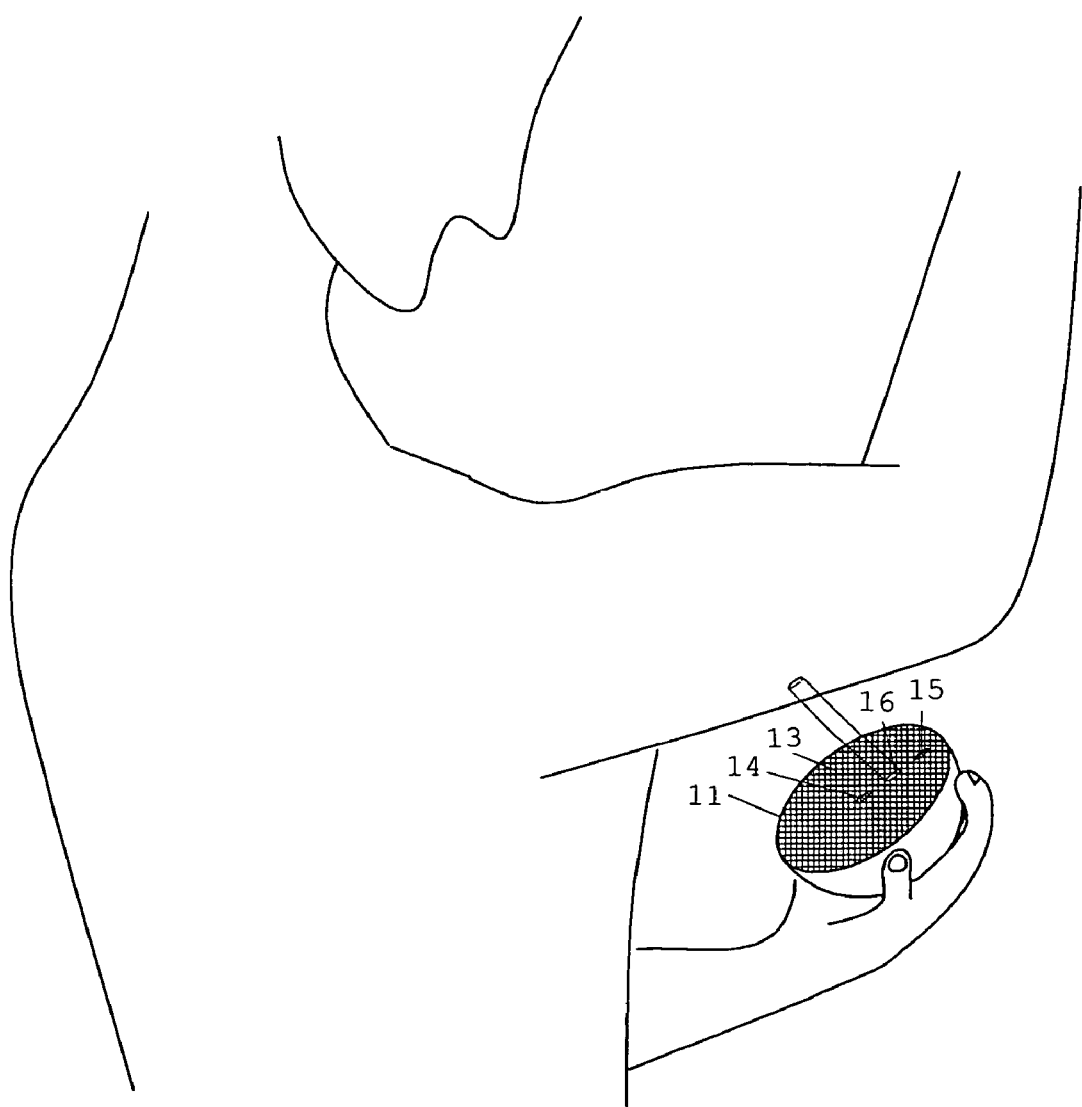
FIG. 2 is a diagram illustrating an alignment method of the optical biological information measuring apparatus according to Embodiment 1 of the present invention.
Figure 3:
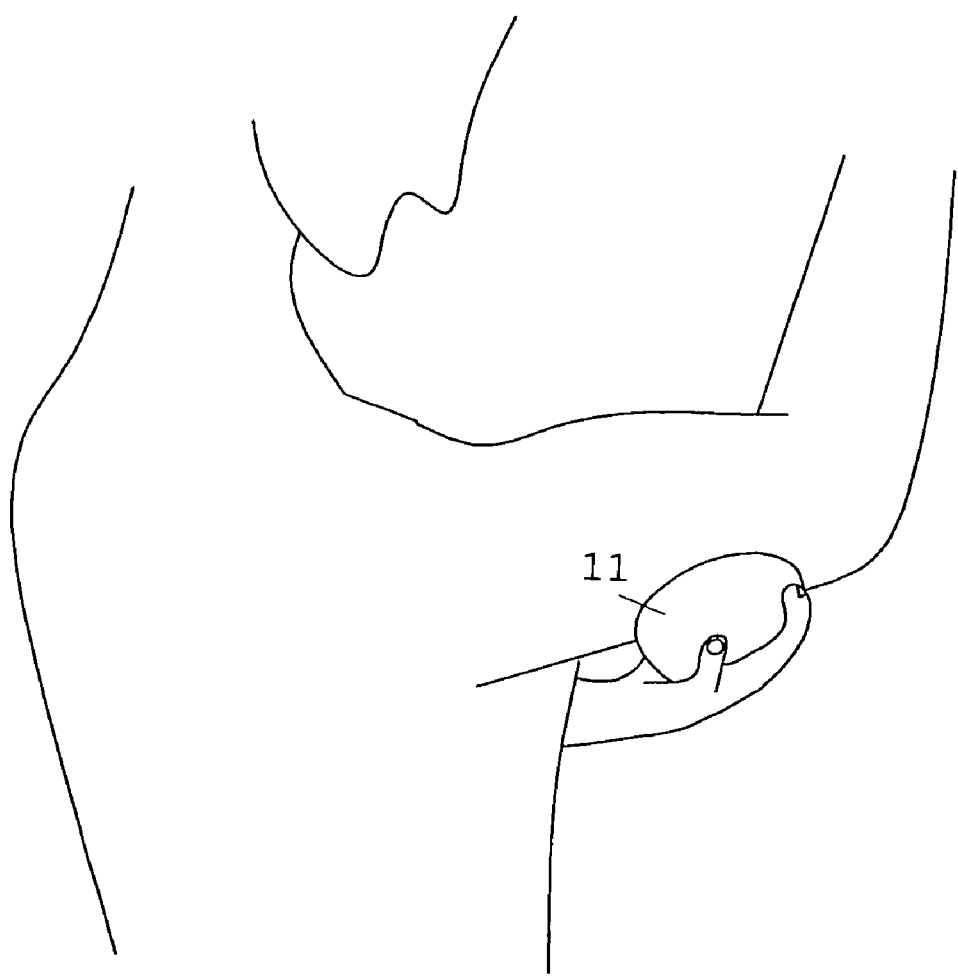
FIG. 3 is a diagram illustrating an alignment method of the optical biological information measuring apparatus according to Embodiments 1 and 5 of the present invention.

FIG. 2 and FIG. 3 illustrate a method of aligning the optical fat thickness gauge 11 of this Embodiment 1 with the back of the upper arm.

As shown in FIG. 2, when measuring the back of the upper arm or the back, the user can align the gauge with a measuring region which cannot be observed directly while watching an image reflected on the measuring surface 13 which corresponds to the measuring region illuminated with visible light emitted from the visible light source 16. In this way, this embodiment allows the user to perform alignment in the measuring region which the user himself/herself cannot directly observe and enables measurements with high measuring repeatability. Here, marking the measuring region on the surface of the living body 12 using a method which does not affect the measurement of the thickness of local fat and aligning visible light emitted from the visible light source 16 with the marked position allows repeated and accurate alignment and allows measurements with higher repeatability.

When the measuring surface 13 of the optical fat thickness gauge 11 is appressed to the living body 12, the attachment is detected by the attachment detection section 17 or the attachment is detected through a variation in an amount of light received by the light-receiving section 14. When the attachment to the living body 12 is detected, the visible light source 16 turns off the light and the LED of the light-emitting section 15 turns on the light. Then, the calculation section 18 calculates the thickness of panniculus which is local biological information based on the amount of near-infrared light emitted from the light-emitting section 15, passed through the living body and received by the light-receiving section 14.

Furthermore, a sound generation section 22 guides the start of measurement, measurement in progress and end of measurement by means of speech, which allows the user to check the progress of measurement without seeing the apparatus. After measurement is completed, the user detaches the optical fat thickness gauge 11 from the measuring region and checks the display section 19, and can thereby perform smooth self-measurement.

Here, if a vibration generation section 23 is provided instead of the sound generation section 22, it is possible to express the progress of measurement by means of vibration and allows quiet measurement. In this case, even hearing-impaired users can use this gauge.

Here, the measuring surface 13 is assumed to be made of a substance which reflects visible light, but it is also possible to make some parts of the measuring surface 13 and optical fat thickness gauge 11 transparent so that the part of the surface of the living body 12 irradiated with light from the visible light source 16 is seen through the body of the optical fat thickness gauge 11.

This allows the user to check the position of the living body 12 irradiated with light from the visible light source 16 up to a place immediately before the optical fat thickness gauge 11 is appressed to the surface of the living body 12, and thereby allows the user to align the measuring surface 13 with the region to be measured more accurately.

Figure 4:
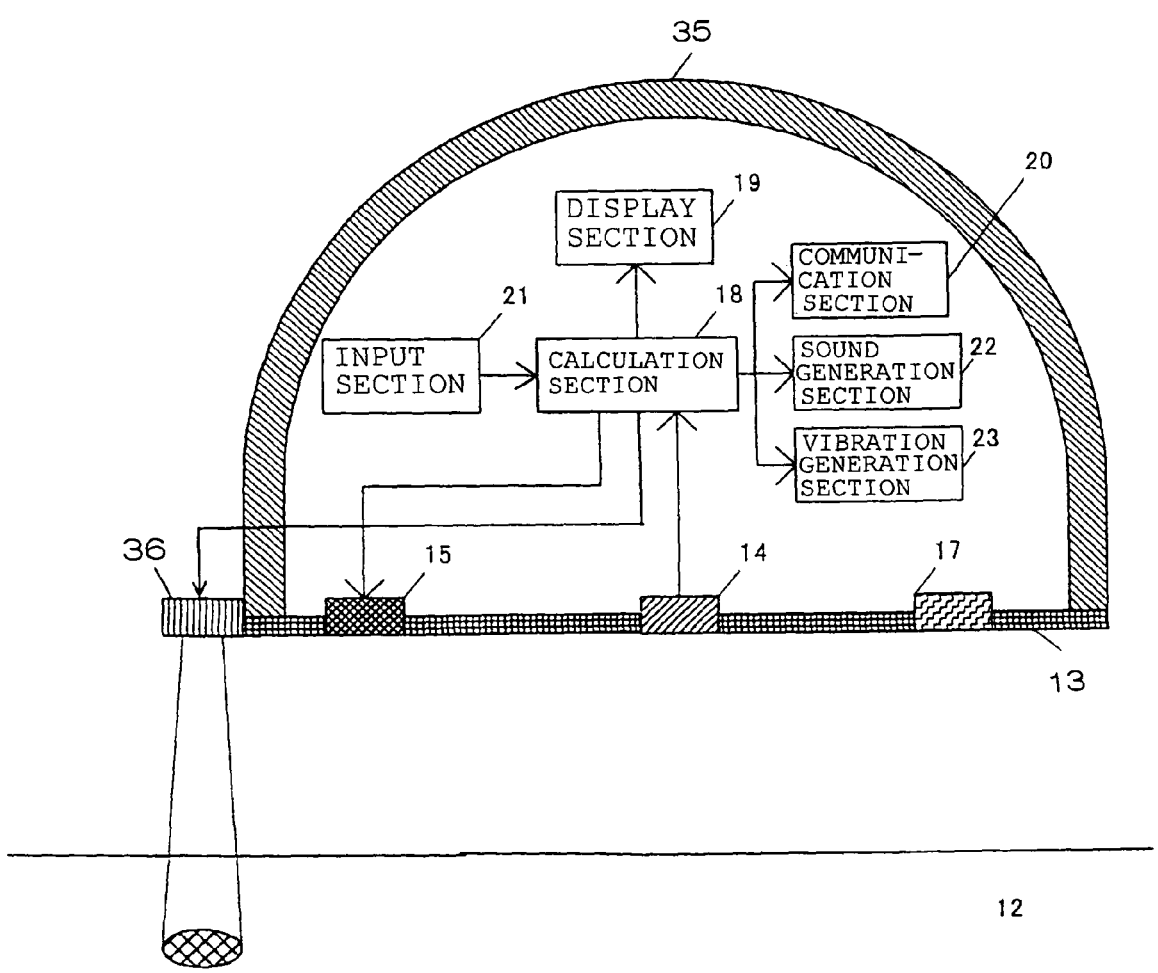
FIG. 4 is a block diagram of the optical biological information measuring apparatus according to Embodiment 1 of the present invention.

FIG. 4 shows a block diagram of an optical fat thickness gauge 35, the position of the visible light source of which is different from that of the optical fat thickness gauge 11 shown in FIG. 1. The same components as those in FIG. 1 are assigned the same reference numerals.

In the optical fat thickness gauge 11 shown in FIG. 1, the visible light source 16 is disposed within the measuring surface 13 between the light-emitting section 15 and light-receiving section 14, but in the optical fat thickness gauge 35 in FIG. 4, a visible light source 36 is disposed at an end of the optical fat thickness gauge 35.

When the optical fat thickness gauge 35 is aligned with a region to be measured of the living body 12, the optical fat thickness gauge 35 is disposed so that the visible light source 36 is oriented in a direction in which the visible light source 36 is visible to the user. This allows the user to check the position of the living body 12 irradiated with light from the visible light source 36 up to a place immediately before the optical fat thickness gauge 35 is appressed to the surface of the living body 12, thus allowing more accurate alignment with the measuring region.

In FIG. 4, the visible light source 36 is disposed outside the measuring surface 13, but the visible light source 36 can also be disposed at an end within the measuring surface 13. Similar effects can be expected in such a case, too.

There may also be a plurality of visible light sources 36 and more accurate alignment of the measuring surface 13 with the measuring region is possible in such a case.

Figure 5:
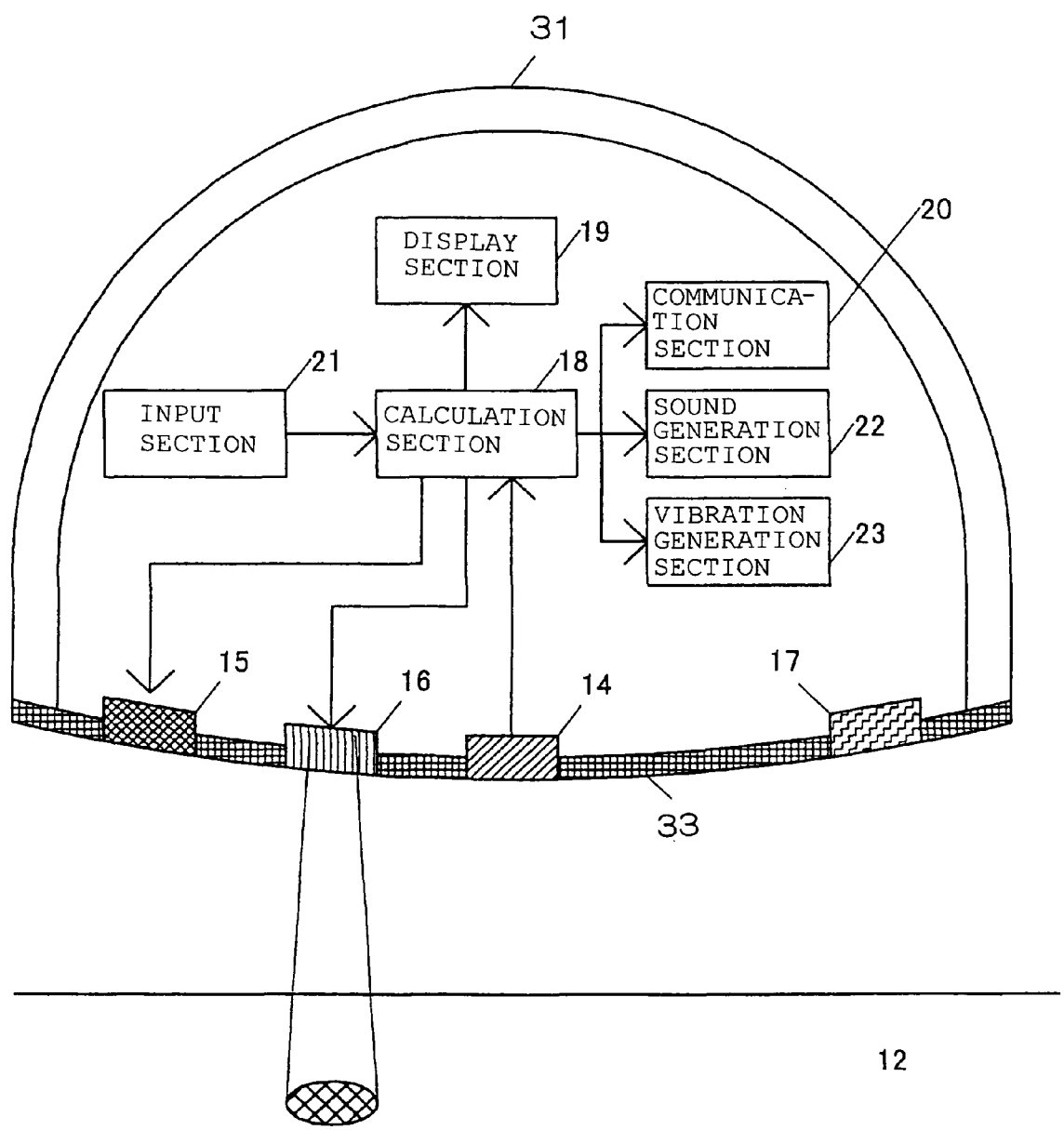
FIG. 5 is a block diagram of the optical biological information measuring apparatus according to Embodiment 1 of the present invention.

FIG. 5 shows a block diagram of an optical fat thickness gauge 31, the shape of the measuring surface of which is different from that of the optical fat thickness gauge 11 shown in FIG. 1. The same components as those in FIG. 1 are assigned the same reference numerals.

Forming a measuring surface 33 having a convex mirrored surface as shown in FIG. 5 makes it possible to reflect a measuring region on the measuring surface 33 in a wide range and makes alignment further easier than in the case of the optical fat thickness gauge 11 shown in FIG. 1.

The optical fat thickness gauge 11 in Embodiment 1 assumes that the wavelength of near-infrared light emitted from the light-emitting section 15 is close to 850 nm, but causing the light-emitting section 15 to emit near-infrared light of two types of wavelength close to 750 nm and 850 nm makes it possible to measure local oxygen concentration as well.

That is, the light-emitting section 15 may be constructed of a first light-emitting body having a peak wavelength close to 750 nm and a second light-emitting body having a peak wavelength close to 850 nm arranged adjoining each other so that light is emitted from these light-emitting bodies continuously or alternately intermittently. The light-receiving section 14 can receive two different amounts of light, a first amount of light when light is emitted from the first light-emitting body and a second amount of light when light is emitted from the second light-emitting body. The absorption ratios of oxidized hemoglobin, reduced hemoglobin, oxidized myoglobin and reduced myoglobin differ drastically between these two wavelengths, and therefore it is possible to measure local oxygen concentration from these two amounts of light received. By aligning the position of the measuring region illuminated with visible light emitted from the visible light source 16 of the present invention while watching the image reflected on the measuring surface 13, it is possible to improve the alignment accuracy at a region that cannot be directly visually observed during self-measurement and measure local oxygen concentration through self-measurement in this case, too.

Moreover, it is also possible to adopt a structure that the light-emitting section 15 is provided with only the second light-emitting body having a peak close to 850 nm and the visible light source 16 is used in place of the first light-emitting body 1. In this case, the wavelength of light emitted by the visible light source 16 is close to 650 nm, and the calculation section 18 can also calculate local oxygen concentration from amounts of light received of these light rays of two wavelengths. In this case, it would be all right if the light-receiving section 14 can receive the light rays of these two wavelengths by causing the visible light source 16 and the second light-emitting body to emit light alternately after alignment by the visible light source 16 is completed. Such a structure can omit the first light-emitting body and thereby measure local oxygen concentration with a simpler structure.

Embodiment 2

Figure 6:
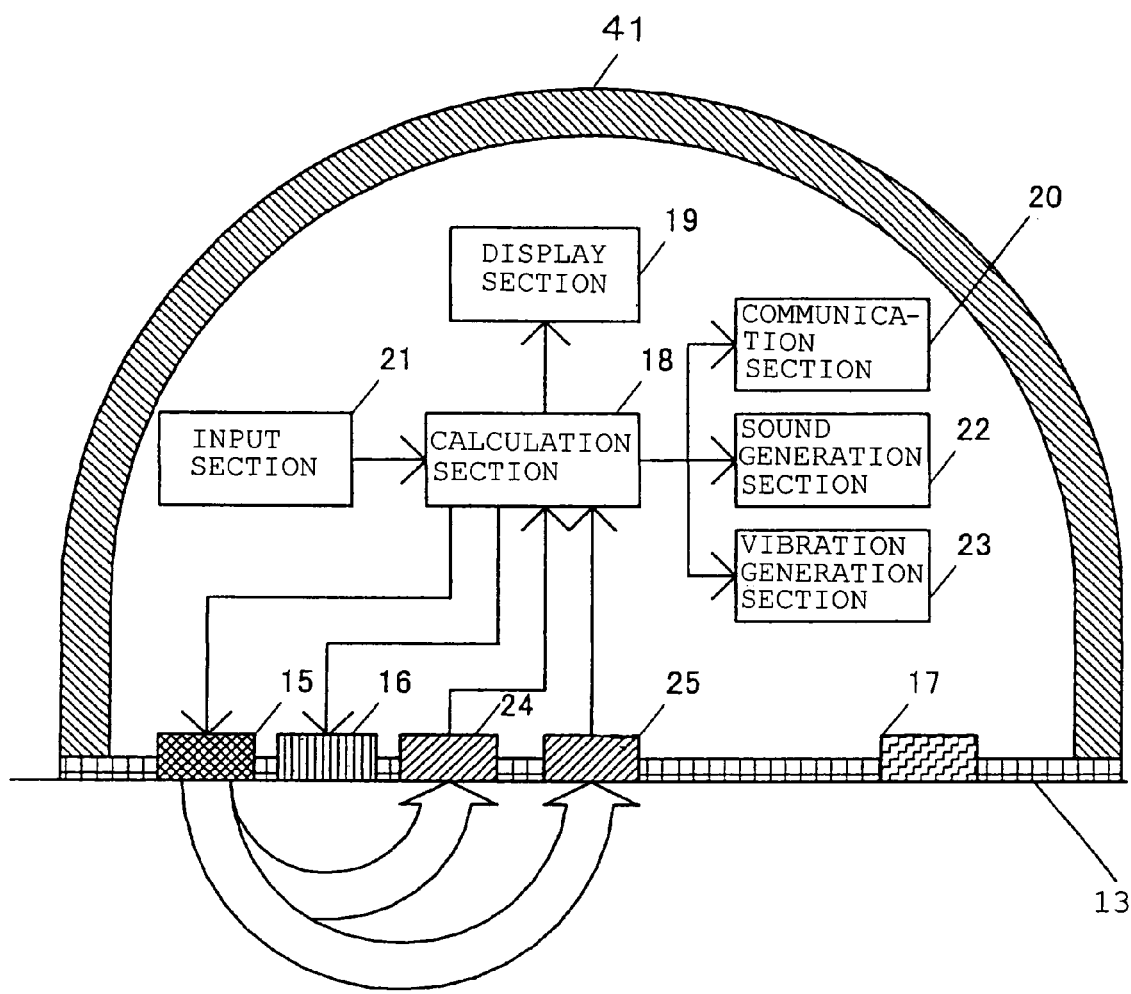
FIG. 6 is a block diagram of an optical biological information measuring apparatus according to Embodiment 2 of the present invention.

FIG. 6 is a block diagram of an optical fat thickness gauge 41 of an optical biological information measuring apparatus according to Embodiment 2 of the present invention. The same components as those in FIG. 1 are assigned the same reference numerals.

While the light-receiving section 14 is disposed at only one position in the optical fat thickness gauge 11 in Embodiment 1, a plurality of light-receiving sections are disposed at different distances from the light-emitting section 15 in the optical fat thickness gauge 41 of this Embodiment 2. Differences from Embodiment 1 will be explained using FIG. 6.

In the optical fat thickness gauge 41 according to this Embodiment 2, a first light-receiving element 24 and a second light-receiving element 25 are disposed within the measuring surface 13 at distances of 15 to 25 mm and 35 to 50 mm from the light-emitting section 15, respectively.

The first light-receiving element 24 and second light-receiving element 25 receive near-infrared light which has been emitted from the light-emitting section 15 and has propagated through the living body. The calculation section 18 calculates the thickness of panniculus from the ratio of two amounts of light received by the first light-receiving element 24 and second light-receiving element 25. In this way, it is possible to measure the thickness of panniculus with variations in the skin color and thickness among individuals corrected.

In this way, the thickness of panniculus (T) can be calculated from the amounts of light received by the two light-receiving elements using the following expression:

$$T = A \cdot X1/X2 + B \qquad \text{(Expression 1)}$$

(A, B denote coefficients, X1, X2 denote amounts of light received by first and second light-receiving elements) Details are described in International Patent Application PCT/JP03/00586 by the applicant, the entire disclosure of which is incorporated herein by reference in its entirety.

Figure 21:
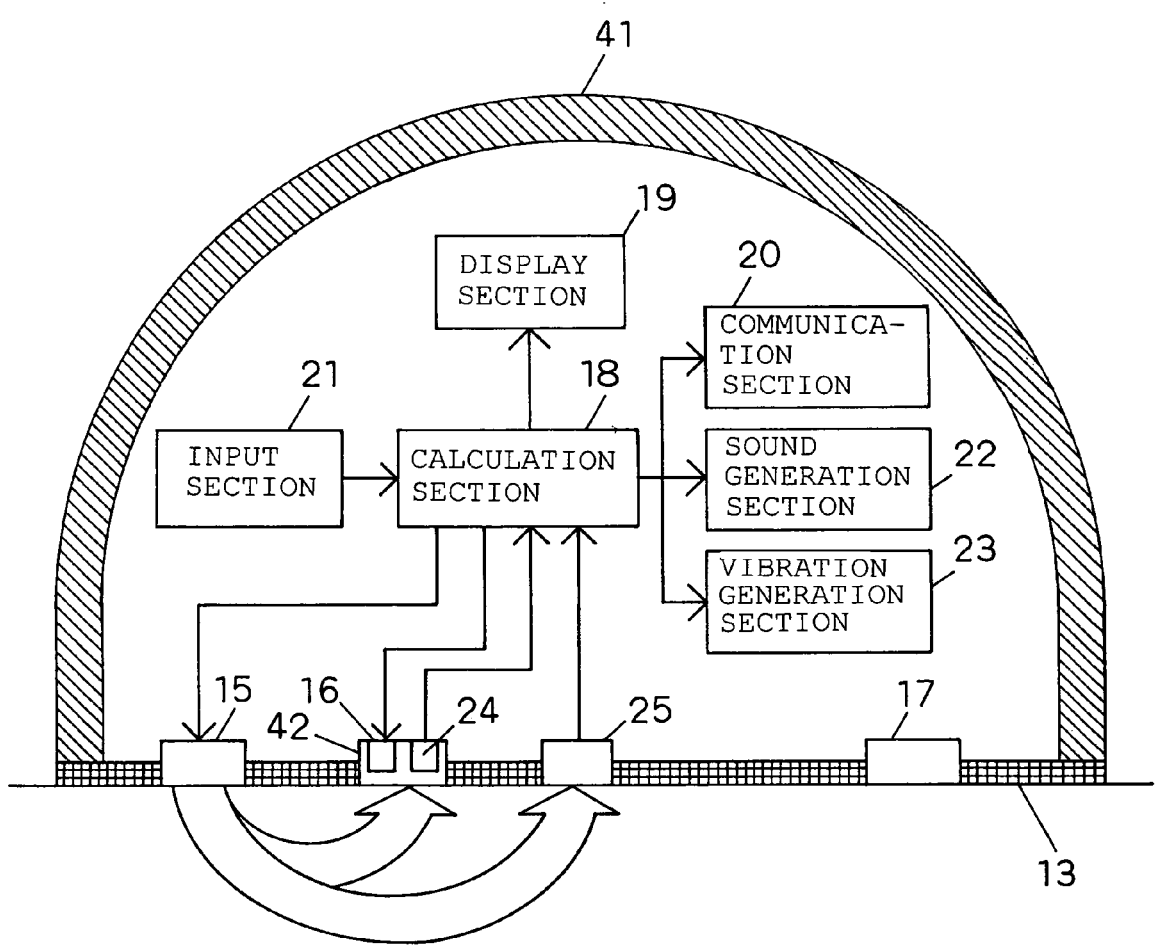
FIG. 21 is a block diagram of an optical biological information measuring apparatus of the present invention.

In this case, the distance from the light-emitting section 15 to the first light-receiving element 24 is preferably substantially equal to the distance from the first light-receiving element 24 to the second light-receiving element 25. FIG. 121 shows an arrangement of the respective elements in such a case. In the optical fat thickness gauge 41 shown in FIG. 21, the visible light source 16 and first light-receiving element 24 are housed in a same housing 42 and this housing 42 is disposed at a substantially midpoint between the light-emitting section 15 and second light-receiving element 25.

When the measuring surface 13 is aligned with the region to be measured of the living body 12, the visible light source 16 turns on the light and when the alignment is completed and measurement is started, the visible light source 16 turns off the light, and therefore even if the visible light source 16 and the first light-receiving element 24 are housed in the same housing 42, no interference occurs between the two.

As described above, the optical biological information measuring apparatus of the present invention has a visible light source which illuminates the measuring region with visible light, and can thereby align the position of the measuring region illuminated with visible light with a mark, thus allowing the user to easily perform alignment with the region of interest.

In Embodiments 1, 2, the measuring surface 13 or 33 is assumed to have a mirrored surface, but the measuring surface 13 or 33 may have a structure reflecting part of visible light. If only the light spot irradiated from the visible light source 16 onto the living body 12 can be checked on the measuring surface 18 or 33, similar effects to those described above can be achieved in that case, too.

Furthermore, the measuring surface 13 or measuring surface 33 may also have the nature of absorbing near-infrared light. In this case, the component of the near-infrared light emitted from the light-emitting section 15 which propagates through an area at a small distance from the surface of the living body 12 is reduced and the accuracy of measuring the thickness of panniculus improves. An example of such a structure of the measuring surface 13 is a structure with a near-infrared cut filter such as UCF-02 manufactured by Kureha Chemical Industry Co., Ltd., superimposed on the mirrored surface.

Furthermore, in Embodiments 1, 2, the visible light source 16 may directly irradiate light onto the living body 12 or may also irradiate light onto the living body 12 through a slit in a ring shape or other appropriate shape. If light is irradiated onto the living body 12 through such a slit, it is possible to identify the position to be measured on the living body 12 more accurately.

Furthermore, the visible light source 16 may be adjusted to be parallel light or may be diffused light. In that case, the light spot becomes smaller as the measuring surface 13 approaches the living body 12, and therefore it is possible to dispose the measuring surface 13 at the position to be measured more accurately.

Furthermore, the measuring surface 13 may also be constructed so as not to reflect light at all. In this case, it is not possible to perform alignment while checking the light spot reflected on the measuring surface 13 irradiated from the visible light source 16 onto the surface of the living body and, but it is possible to achieve effects similar to those described above in the sense that it is possible to perform alignment more accurately than the conventional case by causing the measuring surface 13 to contact the living body 12 while checking the position of the light spot on the living body 12.

In Embodiments 1, 2, the mark in the present invention refers to a light spot irradiated by the visible light sources 16, 36 onto the surface of the living body 12.

Embodiment 3

Figure 7A:
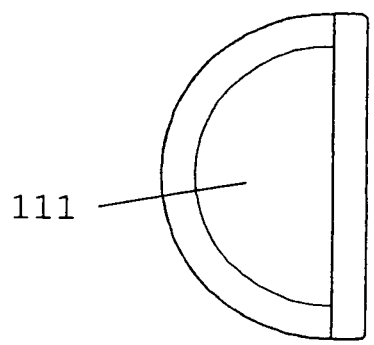
FIG. 7($a$) is an overall view of an optical biological information measuring apparatus according to Embodiment 3 of the present invention.
Figure 7B:
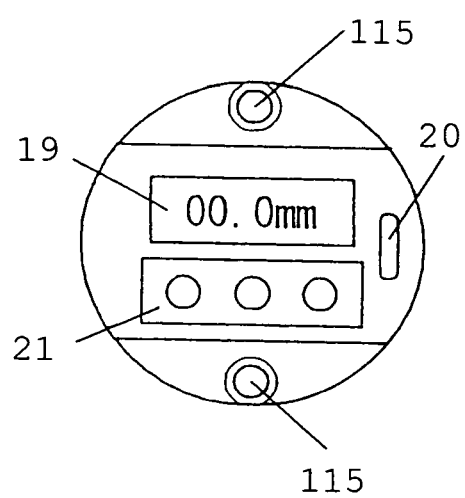
Figure 7C:
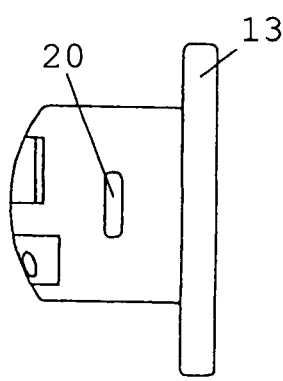
Figure 7D:
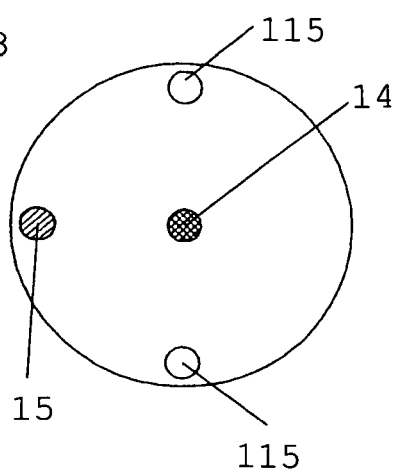
Figure 8A:
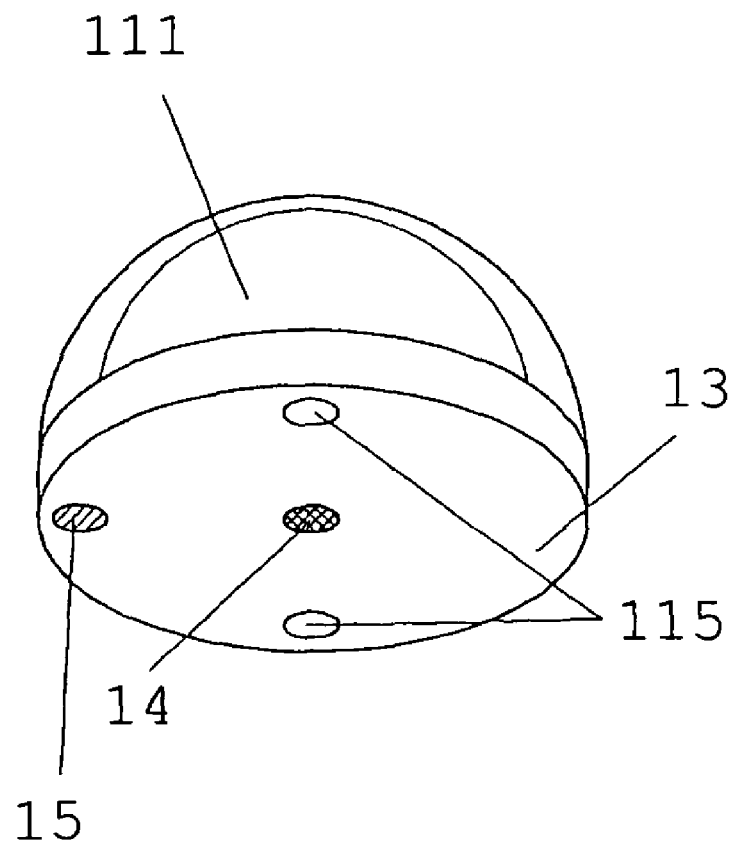
FIG. 8($a$) is a perspective view of the optical biological information measuring apparatus according to embodiment 3 of the present invention.
Figure 9:
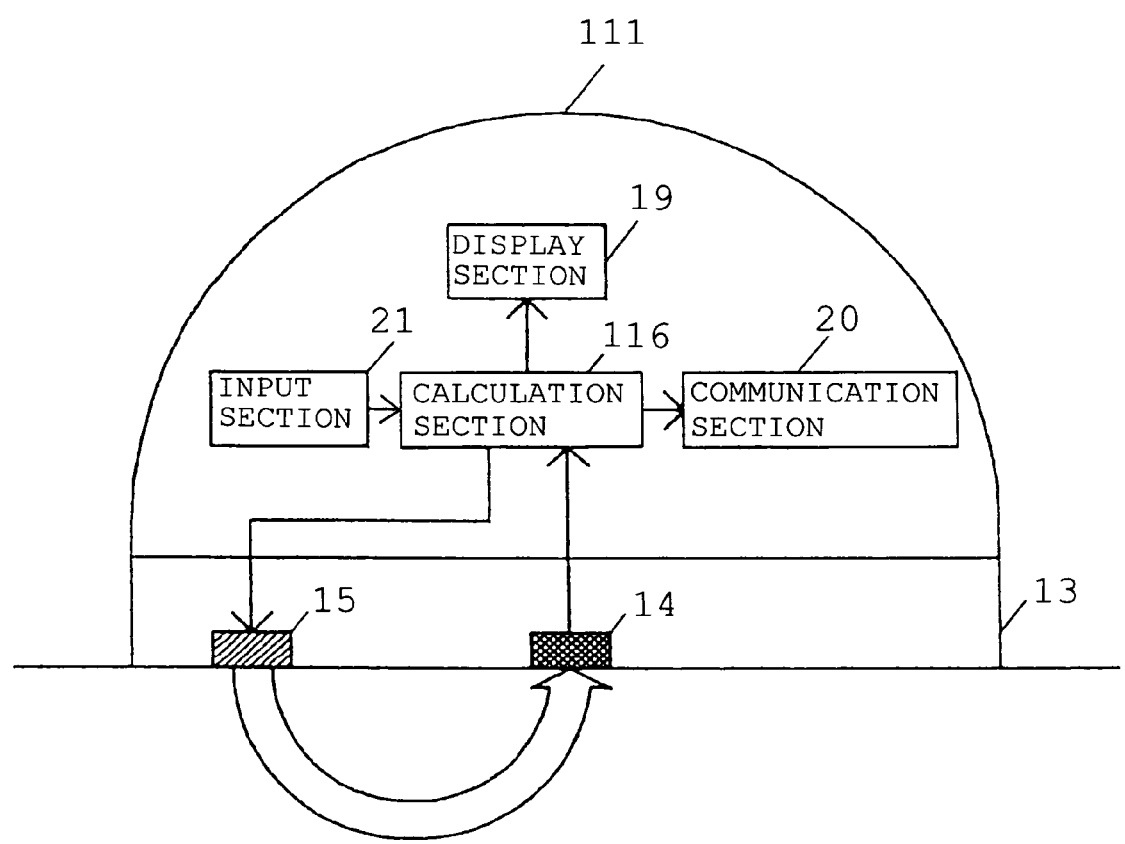
FIG. 9 is a block diagram of the optical biological information measuring apparatus according to Embodiment 3 of the present invention.

FIG. 7(a) is an overall view of an optical fat thickness gauge 111 which is a biological information measuring apparatus according to Embodiment 3 of the present invention, FIG. 7(b) is a top view thereof, FIG. 7(c) is a side view thereof, and FIG. 7(d) is a rear view thereof. Furthermore, FIG. 8(a), (b) are perspective views of the optical fat thickness gauge 111 seen from below and above, respectively and FIG. 9 is a block diagram thereof. A light-receiving section 14 provided with a photodiode is disposed in substantially the center of a measuring surface 13 which contacts a living body 12 and a light-emitting section 15 provided with an LED for irradiating near-infrared light is disposed at a predetermined distance from the light-receiving section 14. Furthermore, through holes 115 are formed at ends of the measuring surface 13 as two alignment sections. The side of the through holes 115 opposite to the side that contacts the living body 12 is tapered in a bowl shape. In this embodiment, the through holes 115 also correspond to an example of the mark creation section of the present invention. A calculation section 116 controls the light-emitting section 15, calculates local biological information such as a thickness of panniculus from a signal obtained from the light-receiving section 14, displays the local biological information obtained on a display section 19 or transmits the local biological information to an external device through a communication section 20. Furthermore, an input section 21 can input information on the sex, age and measuring region, and the calculation section 116 calculates health condition information such as obesity of the living body from the information and local biological information obtained through measurements, displays the information on a display section 19 or transmits the information together with the information on the sex, age and measuring region to the external device through the communication section 20. Adversely, it is also possible to receive information on the sex, age and measuring region from the external device through the communication section 20. Here, using a communication system such as IrDA, USB, and RS-232C for the communication section 20 can improve compatibility with other devices.

Next, an alignment method using the optical fat thickness gauge 111 having the above described structure will be explained. At the time of a first measurement, the optical fat thickness gauge 111 is attached to the surface of the living body 12, two marks are put on the surface of the living body 12 using a pen or seal through the two through holes 115. From a second measurement on, it is possible to perform measurement with high repeatability of alignment by matching the through holes 115 with the marks and visually checking them. Performing alignment at two locations on the surface of the living body 12 makes it possible to ascertain the measuring locations very accurately. Furthermore, using a simple structure such as the through holes 115 reduces the cost. Furthermore, disposing the through holes 115 at ends of the measuring surface 13 reduces the possibility of disturbance light entering the living body 12 through the through holes 115 and being received by the light-receiving section 14. Since the through holes 115 are hole-shaped, unlike a shape with an end of the measuring surface 13 notched, marks never exceed the holes in size while marking, thus allowing accurate alignment.

As an example of preferable dimensions of the optical fat thickness gauge 111 according to this Embodiment 3, the measuring surface 13 is about 100 mm long, the distance between the light-receiving section 14 and light-emitting section 15 is about 45 mm and the diameter of the through hole 115 is about 5 mm.

The through holes 115 are disposed at the ends of the measuring surface 13 according to the above explanation, but any positions may be acceptable unless disturbance light passing through the through holes 115 affects the light-receiving section 14.

However, even if the through holes 115 great positions at which the light-receiving section 14 is affected by the disturbance light, the above described effects of the present invention remain unchanged in performing alignment.

The number of the through holes 115 may be three or more, or adversely the number of the through holes 115 may be one.

In this case, compared to the case with two or more through holes 115, measuring repeatability may decrease but measuring repeatability is still improved when compared to a conventional case where there is no through hole 115.

This embodiment so far has described the case where the through holes 115 constitute the alignment section of the present invention (mark formation section of the present invention), but the alignment section may also have other forms like anotch. In this case, itis inferior to the through holes 115 in terms of the precise alignment described above, but measuring repeatability is improved compared to the conventional structure which is unable to form any marks.

Embodiment 4

Figure 8B:
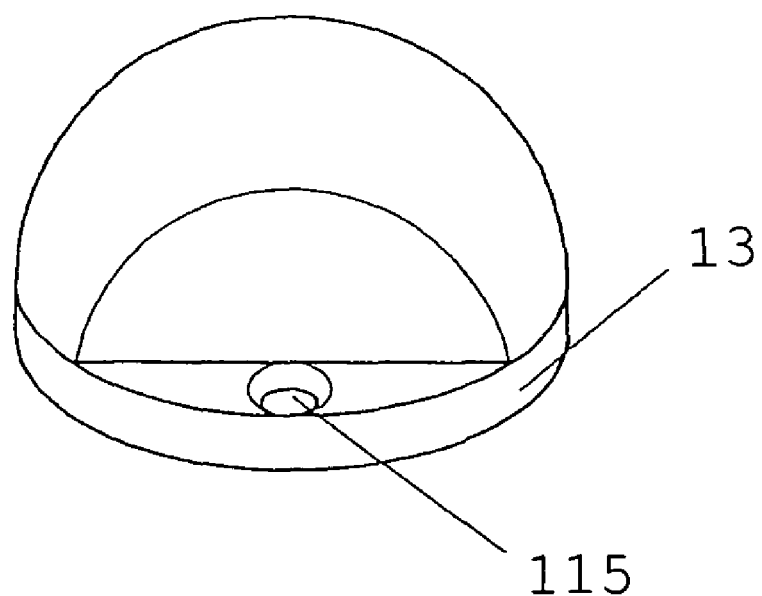
Figure 11B:
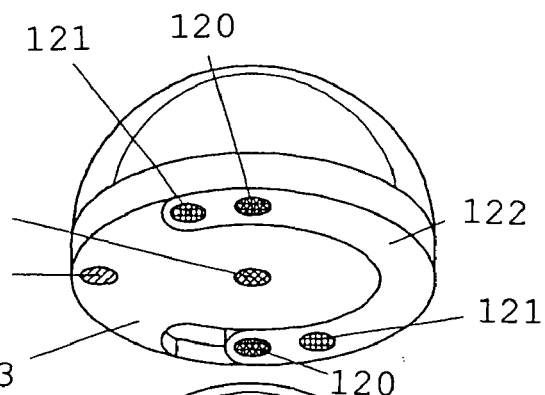
FIG. 11(b) is a perspective view of the optical biological information measuring apparatus according to Embodiment 4 of the present invention.
Figure 11A:
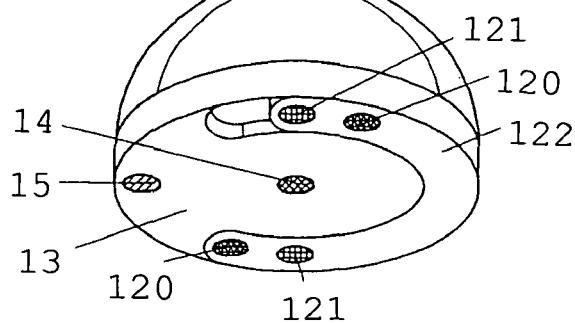
FIG. 11(a) is a perspective view of the optical biological information measuring apparatus according to Embodiment 4 of the present invention.
Figure 12:
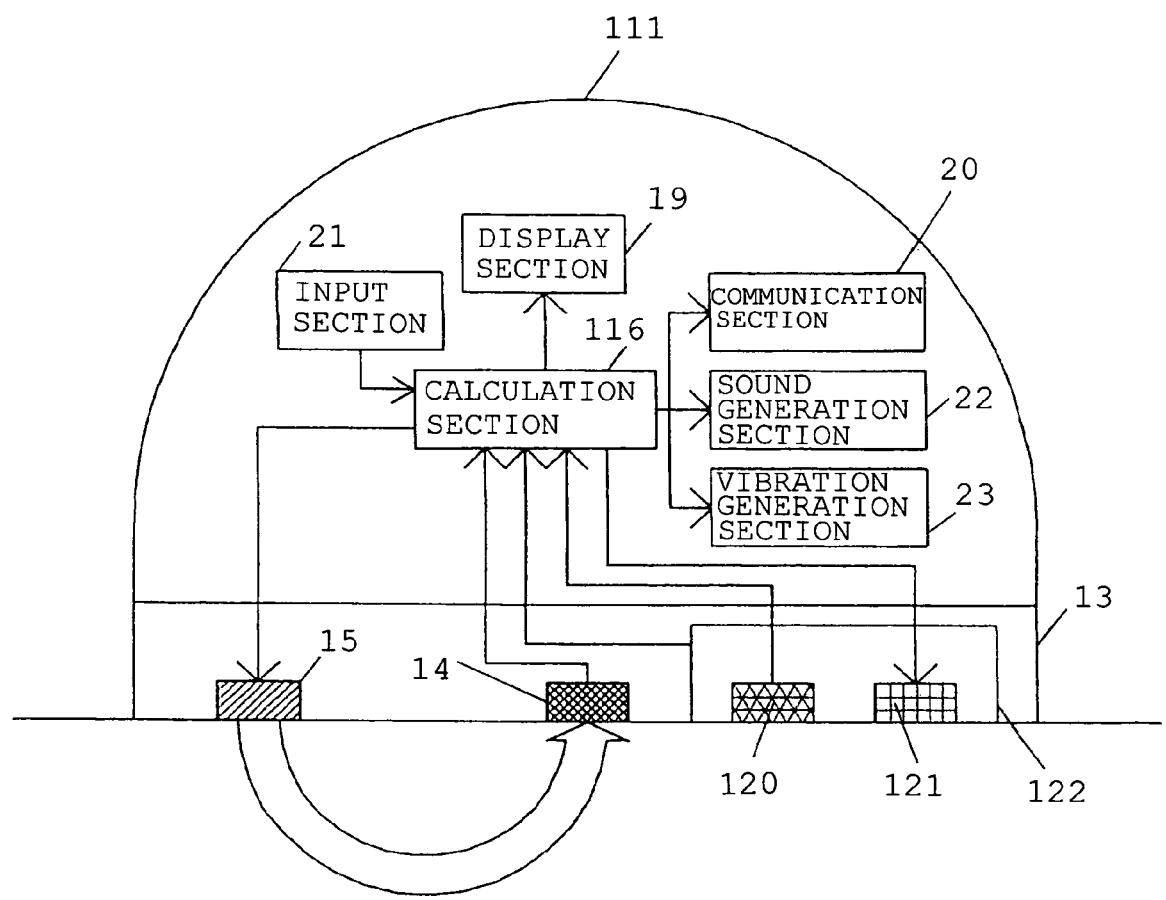
FIG. 12 is a block diagram of the optical biological information measuring apparatus according to Embodiment 4 of the present invention.

FIG. 10(*a*) is an overall view of an optical fat thickness gauge 1111 which is a biological information measuring apparatus according to Embodiment 4 of the present invention, FIG. 10(*b*) is a top view thereof, FIG. 10(*c*) is a side view thereof, and FIG. 10(*d*), FIG. 10(*e*) are rear views thereof. Furthermore, FIG. 11(*a*), (*b*) are perspective views seen from below and FIG. 12 is a block diagram thereof. In FIG. 10(*a*) to (*e*), FIG. 11(*a*), (*b*), FIG. 12, the same components as those in FIG. 7(*a*) to (*d*), FIG. 8(*a*), (*b*), FIG. 9 are assigned the same reference numerals and explanations thereof will be omitted.

An alignment section 120 and a position change mechanism section 122 having a mark creation section 121 are placed at the outer edge of a measuring surface 13. The alignment section 120 includes a light source 123 which emits light having a predetermined wavelength as shown in FIG. 13(*a*) and which is an example of the alignment light source according to the present invention and three optical sensors 124 arranged at equiangular intervals therearound which are sensitive to predetermined wavelengths and which are examples of the light-receiving section of the present invention. The position change mechanism section 122 rotates by, for example, a predetermined angle to switch between the positions of the alignment section 120 and mark creation section 121. The mark creation section 121 marks the surface of the living body 12 using a seal or paint made of a material with a higher absorption factor or reflection factor at a predetermined wavelength compared to the skin of the living body 12. The alignment section 120 decides whether there is a mark 125 right below the alignment section 120 or not.

Figure 15A:
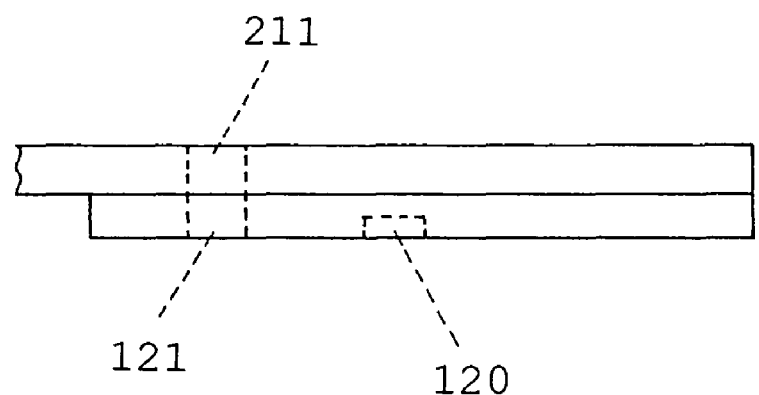
FIG. 15(a) is a diagram illustrating a status of use of the optical biological information measuring apparatus according to Embodiment 4 of the present invention.
Figure 15B:
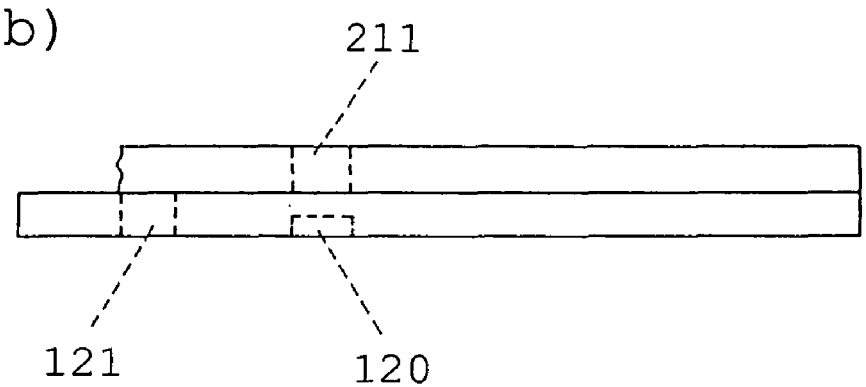
FIG. 15(b) is a diagram illustrating a status of use of the optical biological information measuring apparatus according to Embodiment 4 of the present invention.

Next, an alignment method using the optical fat thickness gauge 1111 according to this embodiment will be explained. First, at the time of a first measurement, as shown in FIG. 10(*d*) and FIG. 11(*a*), measurement is performed by rotating the position change mechanism section 122 so that the mark creation section 121 comes to a predetermined position. Simultaneously with this measurement, the mark creation section 121 puts the mark 125 on the surface of the living body 12. From a second measurement on, as shown in FIG. 10(*e*) and FIG. 11(*b*), the position change mechanism section 122 is rotated so that the alignment section 120 comes to a predetermined position (position of the mark creation section when the mark creation section 121 puts the mark 125) and the measuring surface 13 is aligned with the mark 125 put on the surface of the living body. Here, rotating the position change mechanism section 122 causes the mark creation section 121 to be set to an OFF position so as to perform operation which does not put any unnecessary marks on the surface of the living body 12. Such an operation can be realized through the structure shown in FIG. 15(*a*), (*b*), for example. FIG. 15(*a*), (*b*) are schematic diagrams of a cross section of the optical fat thickness gauge 1111 in the states shown in FIG. 11(*a*), (*b*). That is, when the mark 125 is formed as shown in FIG. 11(*a*), FIG. 15(*a*), a paint supply section 211 matches the mark creation section 121 and a paint is supplied to the mark creation section 121. On the other hand, at the time of alignment as shown in FIG. 11(*b*), FIG. 15(*b*), the paint supply section 211 does not match the mark creation section 121 and the paint is not supplied to the mark creation section 121.

Here, when the mark 125 is right below the alignment section 120 as shown in FIG. 13(*b*), the outputs of the three optical sensors 124 differ from the output at the part of the surface of the living body 12 where the mark 125 is not formed and the output values of these three optical sensors 124 are equal. However, when the position of the alignment section 120 is shifted as shown in FIG. 13(*c*) and FIG. 13(*d*), the output values of these three optical sensors 124 differ from one another. The amounts of change of the output values vary from one sensor to another according to the direction of the displacement. Therefore, the direction of correcting the displacement is determined from the output values of the respective optical sensors 124. By displaying the direction on the display section 19 as shown in FIG. 14(*a*), (*b*), (*c*), (*d*) (*e*), (*f*), (*g*), (*h*), (*i*), (*j*) and (*k*), it is possible to prompt the user to perform alignment. Furthermore, when the correcting direction differs between the two alignment sections 120, the display section 19 shows a sign so that the measuring surface 13 is corrected in the rotational direction. Furthermore, when alignment is achieved, the display on the display section 19 is as shown in FIG. 14 (*l*) or the user is notified by means of sound by a sound generation section 126 or by means of vibration by a vibration generation section 127. In this way, even when it is difficult to see the display section 19, the user can be notified that alignment is achieved by means of speech or vibration. In this way, high accuracy alignment becomes possible at the first measurement and from the second measurement on.

In this way, the optical fat thickness gauge of this embodiment can always perform measurement at the same position, and can thereby measure variations in the thickness of local fat without errors.

In FIG. 14(*a*) to (*l*), only the direction in which the position of the optical fat thickness gauge 1111 should be moved has been shown, but it is also possible to show the direction in which the position of the optical fat thickness gauge 1111 should be moved and the magnitude of the movement in that direction. For example, if the output vectors of the amounts of light of the respective optical sensors 124 are synthesized in proportion to the amounts of light at the respective optical sensors 124, the amount of movement is determined in vector form and it is possible to determine the direction and magnitude of the movement.

Furthermore, alignment may also be decided only through a visual display on the display section 19 or alignment may be decided only by means of speech or alignment may also be decided only by means of vibration. Furthermore, alignment may also be decided by a combination of any of visual display, display with speech and display with vibration. Moreover, alignment may also be decided with displays other than visual, audial displays or vibration. In that case, effects similar to those described above can also be obtained.

This embodiment has described the case where the alignment light-receiving section of the present invention is provided with three optical sensors 124 arranged at uniform intervals around the light source 123, but the number of the optical sensors 124 is not limited to three. Any number of optical sensors 124 can also achieve effects similar to those described above if they are at least arranged at uniform intervals around the light source 123.

Furthermore, in this embodiment of the present invention, even if the optical sensors 124 are not arranged at uniform intervals around the light source 123, the optical sensors 124 can be arranged in any other forms if at least the direction in which the optical fat thickness gauge 1111 should be moved or the direction and magnitude of the movement are determined.

Furthermore, there may be also a case with only one optical sensor 124. In that case, the accuracy is degraded compared to the case with three optical sensors 124, but this embodiment can be considered to achieve effects similar to those described above in the sense that it can perform more accurate alignment than the conventional case.

This embodiment has described the case with two alignment sections 120, but there may be three or more alignment sections 120. Adversely, there can be only one alignment section 120. For example, if only the arrangement direction for the measurement target of the optical fat thickness gauge 1111 is kept track of, it is possible to perform alignment accurately to a certain degree even if there is only one alignment section 120.

Furthermore, similar effects can be achieved by adopting a structure with a mark 125 made of a magnetic substance and the alignment section 120 consisting of three or more magnetic heads as sensors. In this case, the light source 123 of the alignment section 120 becomes unnecessary.

(Relevant Embodiment 1 of the Present Invention)

The following embodiments relate to inventions related the present invention invented by the present inventor.

Figure 16:
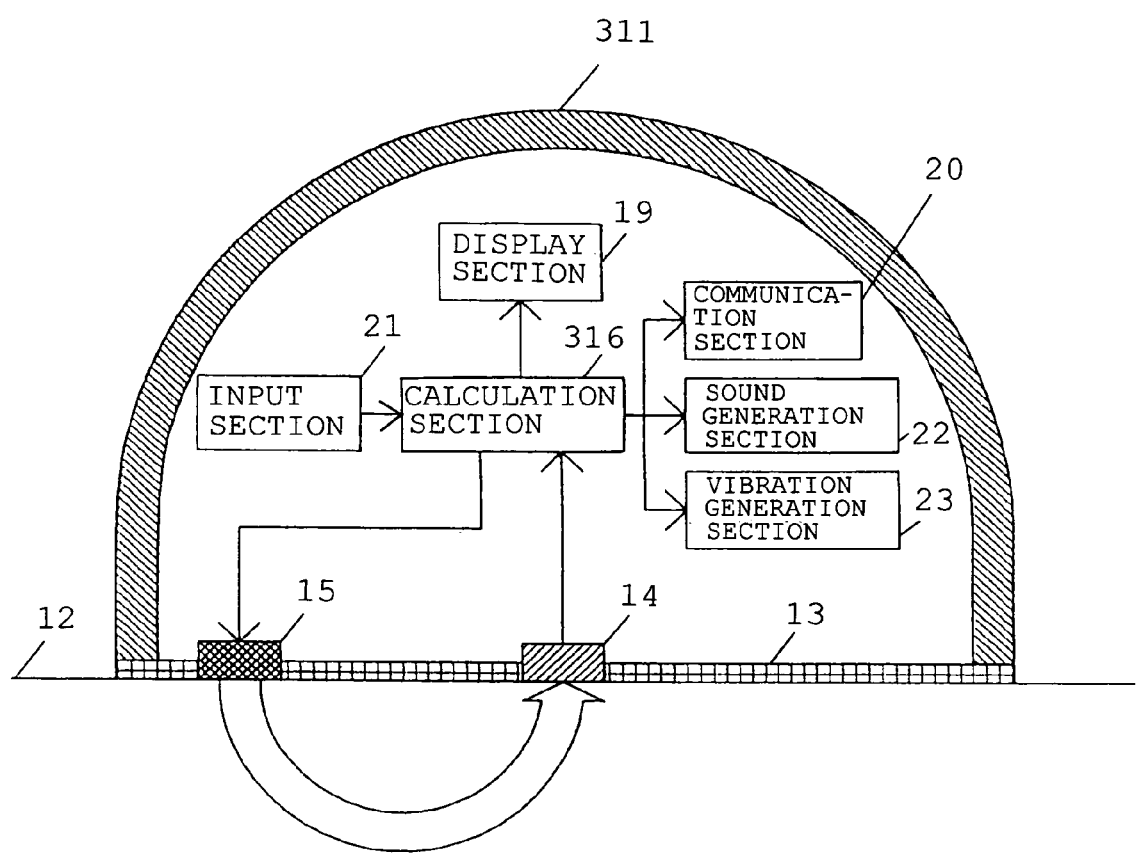
FIG. 16 is a block diagram of an optical biological information measuring apparatus according to Embodiment 1 related to the present invention.

FIG. 16 is a block diagram of an optical fat thickness gauge 311 which is an optical biological information measuring apparatus according to Embodiment 1 related to the present invention. The structure of the optical biological information measuring apparatus in this embodiment together with the operation thereof will be explained using FIG. 16.

In the optical fat thickness gauge 311, a disk-shaped measuring surface 13 having a diameter of approximately 100 mm which contacts a living body 12 is made of a substance which reflects part or the whole of visible light. For example, the measuring surface 13 provides a mirrored surface.

The measuring surface 13 is provided with a light-emitting section 15 including an LED which emits near-infrared light having a wavelength close to 850 nm and a light-receiving section 14 including a photodiode which is an optical sensor which receives light propagating through the living body and reappearing on the surface of the living body 12. Here, the use of light whose central wavelength exists near a wavelength of 800 to 900 nm for the light-emitting section 15 is preferable because the light-emitting section 15 is less affected by fluctuations of the absorption factor due to variations in oxidized/reduced hemoglobin or oxidized/reduced myoglobin and measuring repeatability is improved.

Furthermore, the light-receiving section 14 is disposed almost in the center of the measuring surface 13 and the distance from the light-emitting section 15 is approximately 45 mm. This distance between the light-emitting section 15 and light-receiving section 14 is preferably approximately 35 to 50 mm for measurement of the thickness of panniculus.

A calculation section 316 calculates local biological information such as a thickness of panniculus from a signal obtained from the light-receiving section 14. The calculation section 316 displays the local biological information obtained on a display section 19 or sends the signal to an external device through a communication section 20.

Other components similar to those shown in FIG. 1 are assigned the same reference numerals and explanations thereof will be omitted.

Figure 17:
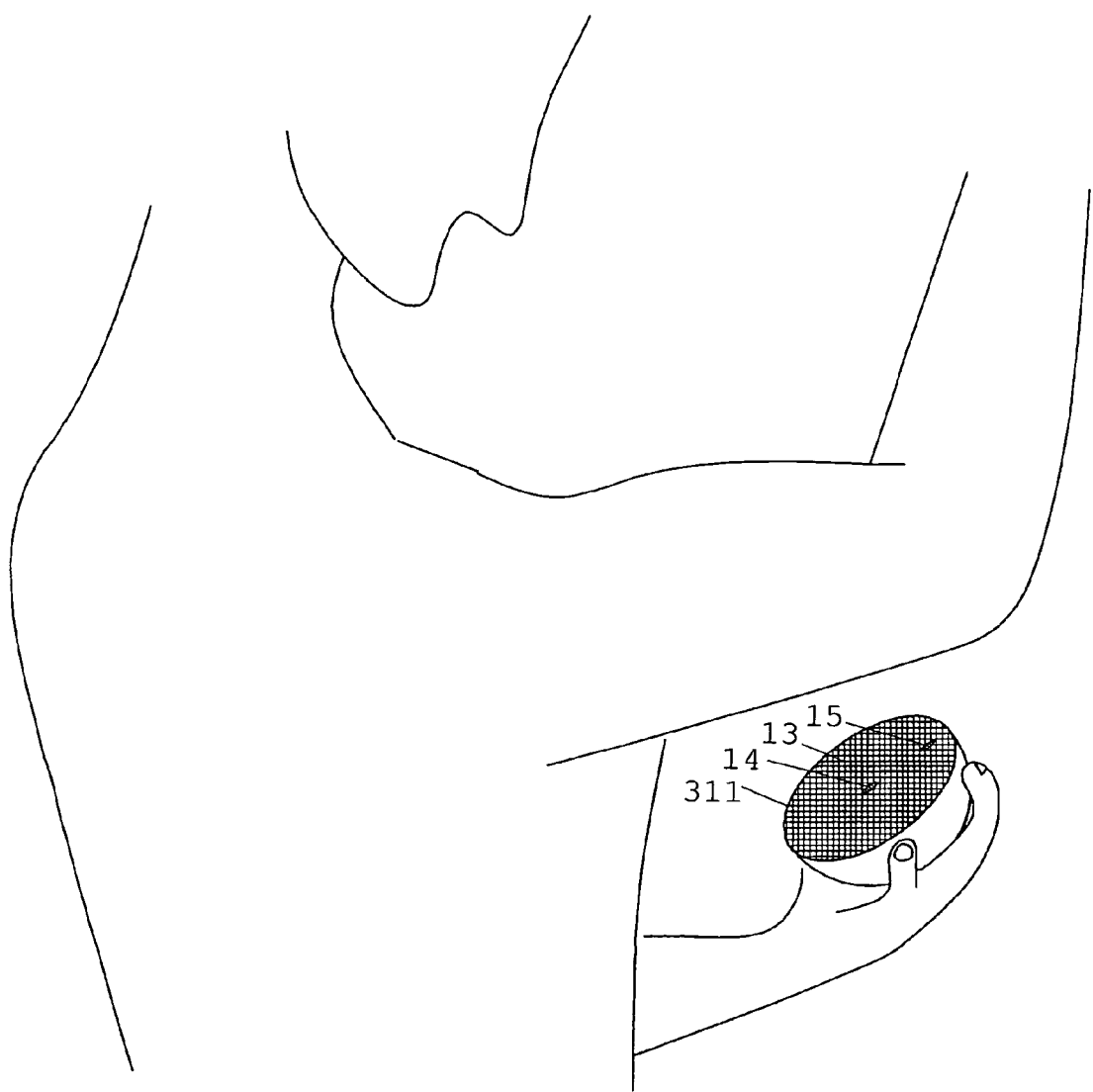
FIG. 17 is a diagram illustrating an alignment method of an optical biological information measuring apparatus according to Embodiment 2 related to the present invention.

Next, a method of alignment of the optical biological information measuring apparatus according to this embodiment with the measuring region will be explained. FIG. 17 and FIG. 3 show the method of aligning the optical fat thickness gauge 311 of this embodiment with the back of the upper arm.

As shown in FIG. 17, when measuring the back of the upper arm or the back, after aligning the gauge with a measuring region which cannot be observed directly while watching an image reflected on the measuring surface 13, the user brings the optical fat thickness gauge 311 closer to the measuring region, causes the gauge to contact the measuring region and performs measurement as shown in FIG. 3. In this way, this embodiment allows the user to perform alignment of the measuring region which the user himself/herself cannot directly observe, and thereby enables measurements with high measuring repeatability. In the alignment shown in FIG. 17, alignment with the region to be measured becomes easier by observing the image reflected on the measuring surface 13 relative to the position of the light-emitting section 15 or light-receiving section 14. At this time, the region to be measured preferably contacts a midpoint between the light-emitting section 15 and light-receiving section 14. Therefore, a reference for alignment may be provided at a midpoint between the light-emitting section 15 and light-receiving section 14.

Next, an optical biological information measuring apparatus according to this embodiment having a structure different from that shown in FIG. 16 will be explained.

Figure 18:
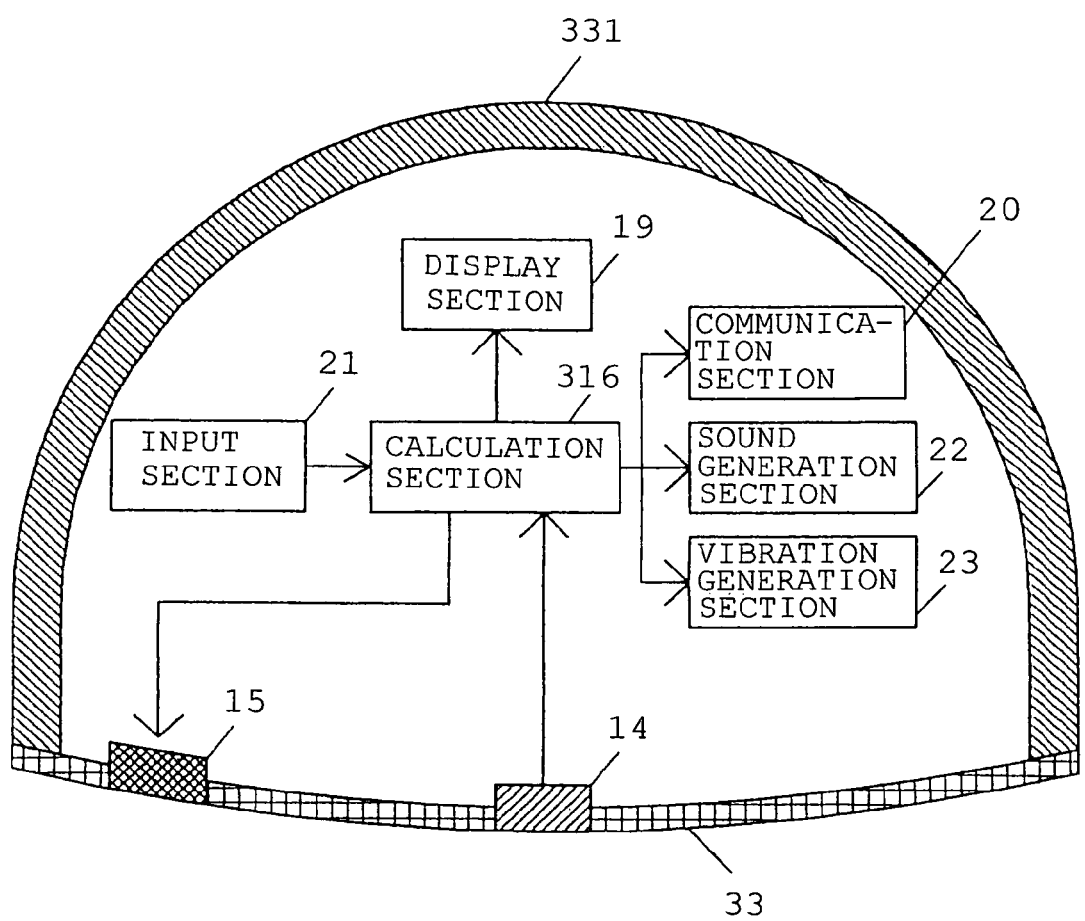
FIG. 18 is a block diagram of the optical biological information measuring apparatus according to Embodiment 1 related to the present invention.

FIG. 18 shows a block diagram of an optical fat thickness gauge 331 having a measuring surface shape different from that of the optical fat thickness gauge 311 shown in FIG. 16. The same components as those in FIG. 16 are assigned the same reference numerals.

Unlike the measuring surface 13 of the optical fat thickness gauge 311 having a flat shape, the measuring surface 33 of the optical fat thickness gauge 331 has a convex-shaped mirrored surface, can reflect a wide range of the measuring region on the measuring surface 33 and further facilitates alignment compared to the case with the optical fat thickness gauge 311 shown in FIG. 16.

The optical fat thickness gauge 311 according to this embodiment assumes that the wavelength of near-infrared light emitted from the light-emitting section 15 is a wavelength close to 850 nm, but as explained in Embodiment 1, it is also possible to cause the light-emitting section 15 to emit near-infrared light of two types of wavelength; wavelength close to 750 nm and wavelength close to 850 nm to thereby measure local oxygen concentration as well.

(Relevant Embodiment 2 of the Present Invention)

Figure 19:
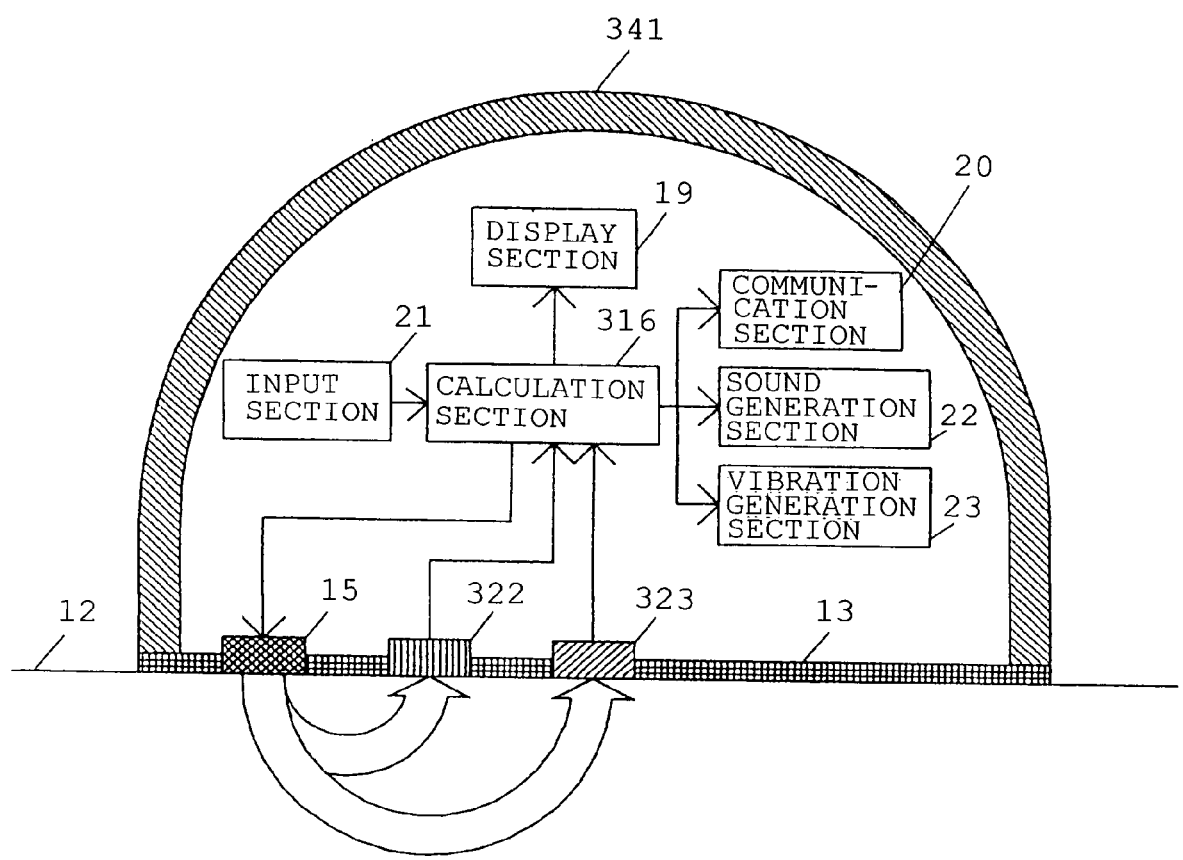
FIG. 19 is a block diagram of the optical biological information measuring apparatus according to Embodiment 2 related to the present invention.
Figure 20:
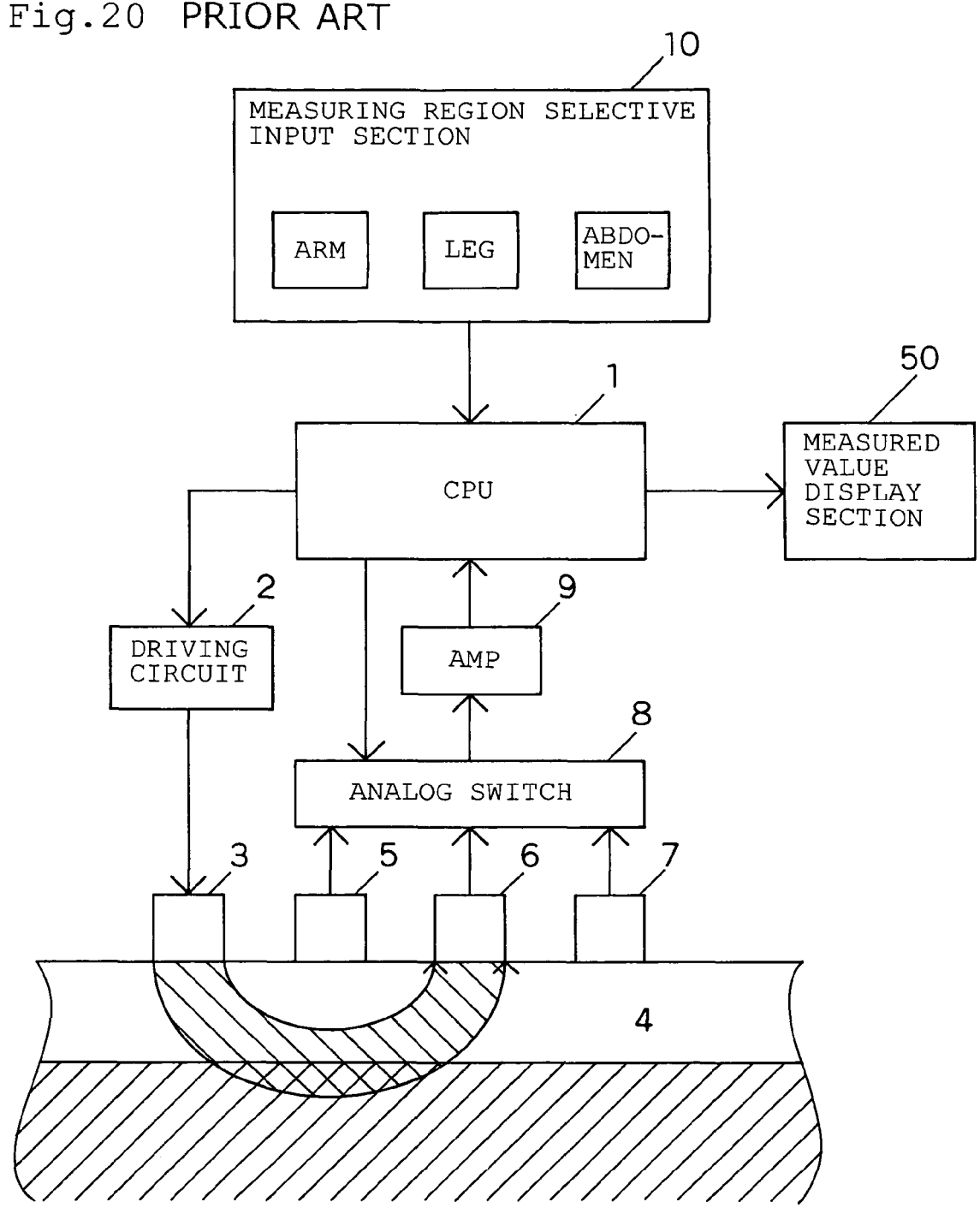
FIG. 20 is a block diagram of a conventional optical biological information measuring apparatus.

FIG. 19 is a block diagram of an optical fat thickness gauge 341 which is an optical biological information measuring apparatus according to Embodiment 2 related to the present invention. The same components as those in FIG. 16 are assigned the same reference numerals.

While only one light-receiving section 14 is disposed in the optical fat thickness gauge 311 according to Relevant Embodiment 1 of the present invention, the optical fat thickness gauge 341 according to this Embodiment 2 has a plurality of light-receiving sections at different distances from the light-emitting section 15. Differences from Embodiment 1 related to the present invention will be explained using FIG. 19.

In the optical fat thickness gauge 341 according to this embodiment, a first light-receiving element 322 and a second light-receiving element 323 are disposed within the measuring surface 13 as the light-receiving sections at distances of approximately 15 to 25 mm and approximately 35 to 50 mm from the light-emitting section 15, respectively.

The first light-receiving element 322 and second light-receiving element 323 each receive near-infrared light which has been emitted from the light-emitting section 15 and has propagated through the living body. The calculation section 316 calculates the thickness of panniculus from the ratio of two amounts of light received by the first light-receiving element 322 and second light-receiving element 323. In this way, it is possible to measure the thickness of panniculus with variations in the skin color and thickness among individuals corrected.

In Relevant Embodiments 1, 2 of the present invention, the entire surface of the measuring surface 13 of the optical biological information measuring apparatus reflects visible light, but the embodiments may also be constructed so that only part of the measuring surface 13 which is visible to the user can reflect visible light.

Furthermore, if the measuring surface 13 also has the nature of absorbing near-infrared light, the component of the near-infrared light which propagates through an area at a small distance from the surface of the living body 12 is reduced and the accuracy of measuring the thickness of panniculus improves. An example of such a structure of the measuring surface 13 is a structure with a near-infrared cut filter such as UCF-02 manufactured by Kureha Chemical Industry Co., Ltd., superimposed on the mirrored surface.

As described above, using the optical biological information measuring apparatus of this embodiment prevents displacement in every measurement even if the measuring region cannot be directly visually checked and improves measuring repeatability.

Relevant Embodiments 1, 2 of the present invention relate to an optical biological information measuring apparatus comprising a measuring surface to be contacted to the living body, at least part of which reflects part or the whole of visible light, a light-emitting section disposed on the measuring surface, which irradiates light of a predetermined wavelength and a light-receiving section disposed on the measuring surface, which receives light irradiated onto the surface of the living body and propagated through the living body. Such an optical biological information measuring apparatus allows the user to measure local biological information which cannot be easily measured by the user himself/herself.

In the optical biological information measuring apparatus according to the foregoing embodiments, each calculation section calculates local biological information based on the amount of light received by the light-receiving section, but the apparatus can also be adapted so that only information on the amount of light received by the light-receiving section is sent and the optical biological information measuring apparatus does not calculate local biological information. In this case, the information on the amount of light received to be transmitted from the communication section 20 is received by an external device such as a personal computer and the external device calculates and displays the local biological information.

Furthermore, it is also possible adapt the embodiment so that the local biological information calculated by the external device is sent to the optical biological information measuring apparatus of the present invention and the local biological information received by the communication section 20 is displayed on the display section 19. In this way, causing the external device to calculate local biological information makes it possible to easily change the calculation method or change data necessary for calculation.

In the above described explanations, each light-emitting section outputs near-infrared light or visible light, but the light-emitting section may also output light of other wavelengths to measure biological information.

Figure 22:
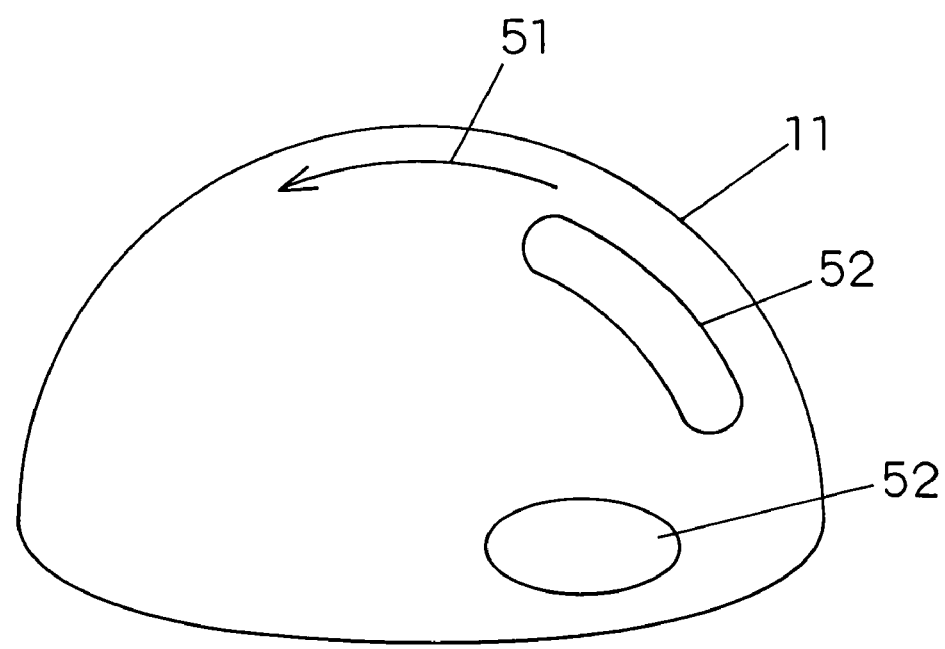
FIG. 22 is a perspective view of the optical biological information measuring apparatus of the present invention.

In the explanations so far, each optical fat thickness gauge may also include a mark 51 indicating the direction of placement on the living body 12 and a recess 52 formed so as to fit into the shape of a finger to determine the direction of holding the gauge as shown in FIG. 22, for example. Such a structure allows the measuring surface 13 to contact the region to be measured of the living body 12 more accurately. For example, if the mark 51 is predetermined as in the longitudinal direction of the body, it is possible to reduce variations in measurement due to the direction of placement of the measuring surface 13 on the living body 12.

Figure 23:
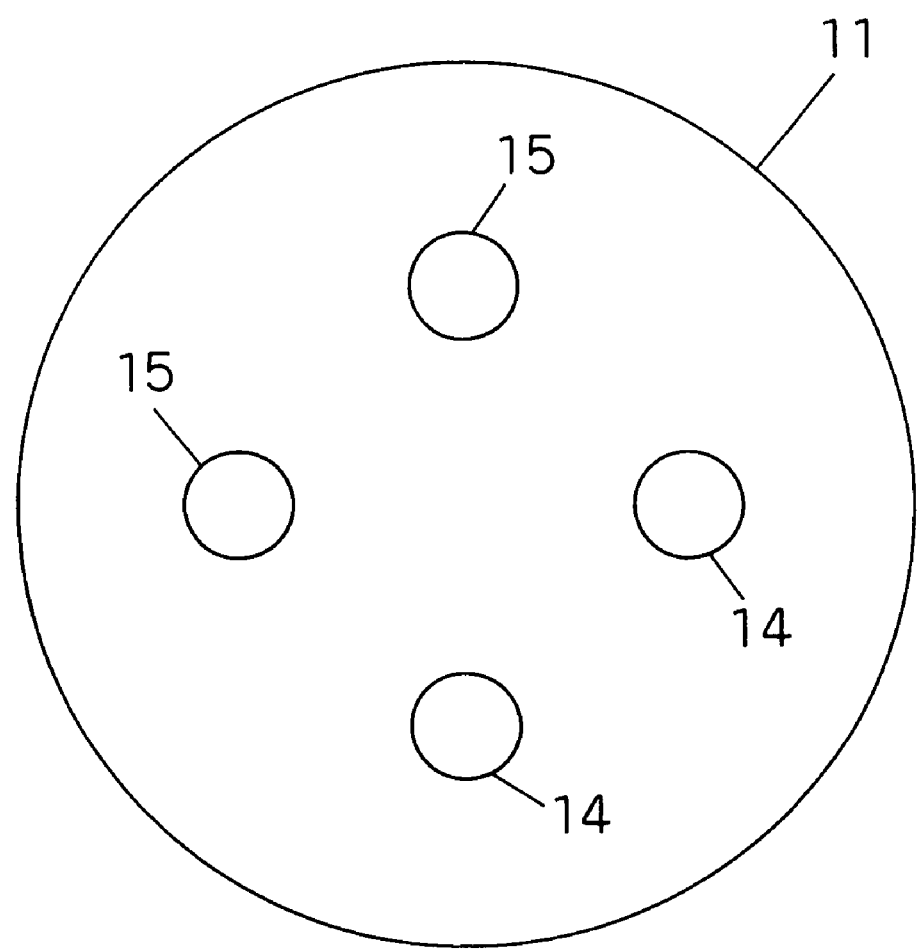
FIG. 23 is a rear view of the optical biological information measuring apparatus of the present invention.

To further reduce variations in measurement due to the direction of placement of the measuring surface 13 on the living body 12, it is also possible to place a plurality of light-emitting sections 15 and light-receiving sections 14 on the measuring surface 13 as shown in FIG. 23 and calculate the thickness of fat from an average of amounts of light received by the respective light-receiving sections 14.

Furthermore, the biological information measuring apparatus of the present invention explained so far is not limited to the fat thickness measuring apparatus or local tissue oxygen concentration measuring apparatus, but may also be applicable to an apparatus of measuring other biological information.

The description of dimensions explained so far is merely an example and of course, other dimensions may also be used.

The program of the present invention is a program for causing a computer to execute the function of part or the whole of means (or apparatus) of the above described biological information measuring apparatus of the present invention and a program which operates in cooperation with the computer.

Furthermore, the recording medium of the present invention is a recording medium which stores a program for causing a computer to execute the function of part or the whole of means (or apparatus) of the above described biological information measuring apparatus of the present invention and a computer-readable recording medium whereby the read program executes the function in cooperation with the computer.

The term "part or the whole of means (or apparatus)" of the present invention means one or some means of the plurality of means.

The term "function of means (or apparatus)" of the present invention means the function of the whole or part of the means.

Furthermore, one mode of usage of the program of the present invention may be a mode in which the program is recorded in a computer-readable recording medium to operate in cooperation with the computer.

Furthermore, one mode of usage of the program of the present invention may be a mode in which the program is transmitted in a transmission medium, read by a computer and operates in cooperation with the computer.

Furthermore, the recording medium may include ROM, etc., and the transmission medium may include a transmission medium such as the Internet, light, radio wave and sound wave, etc.

Furthermore, the above described computer is not limited to pure hardware such as a CPU, but may also include firmware, OS or one that includes peripheral devices.

As described above, the structure of the present invention may be implemented by software or hardware.

The optical biological information measuring apparatus according to the present invention can measure biological information with high alignment accuracy and is useful as a fat thickness measuring apparatus, etc.

What is claimed is:

1. An optical biological information measuring apparatus comprising:
   a measuring surface to be placed on a surface of a living body;
   a visible light source which irradiates a first light to the living body to illuminate a position of the living body to be measured, the visible light source turning off irradiation of the first light to the living body after the measuring surface has contacted the surface of the living body, said first light being visible light;
   a light-emitting section which irradiates the surface of the living body with a second light, said second light being light of a predetermined wavelength;
   a light-receiving section which receives the second light irradiated onto and returned from the surface of the living body; and
   a contact detection section which detects that said measuring surface has contacted the surface of the living body, and is configured to cause said visible light source to turn off the irradiation of the first light upon detection that said measuring surface has contacted the surface of the living body,
   wherein said measuring surface being formed with said visible light source, said light-emitting section, said light-receiving section, and said contact detection section which are arranged in side-by-side relation along said measuring surface.

2. The optical biological information measuring apparatus according to claim 1, wherein said visible light source is placed at an end of said measuring surface.

3. The optical biological information measuring apparatus according to claim 1, wherein said contact detection section decides that said measuring surface has contacted the surface of the living body based on a variation in an amount of light received by said light-receiving section and/or by detecting attachment between said measuring surface and the living body.

4. The optical biological information measuring apparatus according to claim 1, wherein a color of said first light irradiated by said visible light source is red.

5. The optical biological information measuring apparatus according to claim 1, wherein part of the surface of said measuring surface reflects at least a part of the first light.

6. The optical biological information measuring apparatus according to claim 5, wherein said measuring surface includes a mirrored surface.

7. The optical biological information measuring apparatus according to claim 1, further comprising a calculation section which calculates a thickness of local fat based on an amount of the light received by said light-receiving section.

8. The optical biological information measuring apparatus according to claim 7, wherein said light-receiving section comprises two light-receiving elements arranged at different distances from said light-emitting section for receiving the light; and said calculation section calculates the thickness of local fat from a ratio of two amounts of light received by said two light-receiving elements based on a following expression:

$$T = A \cdot X1/X2 + B$$

(A, B denote coefficients, X1, X2 denote amounts of light received by first and second light-receiving elements).

9. The optical biological information measuring apparatus according to claim 1, wherein said light-emitting section can emit light of two types of wavelength;
   said light-receiving section can receive the light of two types of wavelength; and
   said optical biological information measuring apparatus further comprises a calculation section which calculates local tissue oxygen concentration from the ratio of the respective amounts of light having the two types of wavelengths received by said light-receiving section.

10. The optical biological information measuring apparatus according to claim 9, wherein the light of two types of wavelength is light having a wavelength including substantially 650 nm and light having a wavelength including substantially 850 nm.

11. The biological information measuring apparatus according to claim 1, wherein said light-receiving section can receive the first light output from said visible light source and the second light, and
   said biological information measuring apparatus further comprises a calculation section which calculates local tissue oxygen concentration from a ratio of amounts of the first light received by said light-receiving section and that of the second light received by said light-receiving section.

12. A program stored on a non-transitory computer readable medium for causing a computer to function as a calculation section which calculates the thickness of local fat based on an amount of light received by said light-receiving section of the optical biological information measuring apparatus according to claim 8.

13. The optical biological information measuring apparatus according to claim 1, further comprising one or more through holes formed on said measuring surface.

14. The optical biological information measuring apparatus according to claim 13, wherein said through hole is placed at a position at which said light-receiving section receives no influence from outside light through said through hole.

15. An optical biological information measuring method comprising:
   placing a measuring surface near a surface of a living body;
   irradiating a first light from a visible light source arranged along said measuring surface to the living body to illuminate a position of the living body to be measured, said first light being visible light;
   detecting whether or not said measuring surface has contacted the surface of the living body by a contact detection section arranged along said measuring surface,
   turning off the irradiation of the first light to the living body responsive to detection that the measuring surface has contacted the surface of the living body by the contact detection section;
   irradiating the surface of the living body with a second light, said second light being light having a predetermined wavelength; and
   receiving the second light irradiated onto and returned from the surface of the living body.

16. The optical biological information measuring apparatus according to claim 1, wherein said light irradiated from said light-emitting section is near-infrared light.

17. The optical biological information measuring apparatus according to claim 16, wherein at least part of said measuring surface absorbs near-infrared light irradiated from said light-emitting section.

18. The optical biological information measuring apparatus according to claim 5, wherein said measuring surface is convex-shaped.

19. The optical biological information measuring method according to claim 15, wherein said aligning the measuring surface with the mark displayed on the surface of the living body comprises aligning the measuring surface which reflects at least a part of the first light while watching the surface of the living body reflected on said measuring surface.

20. The optical biological information measuring apparatus according to claim 1, wherein the light-emitting section turns off irradiation of the second light to the living body when the measuring surface is not in contact with the surface of the living body.

21. The optical biological information measuring method according to claim 15, further comprising turning off irradiation of the second light to the living body when the measuring surface is not in contact with the surface of the living body.

22. The optical biological information measuring apparatus according to claim 1, wherein said visible light source is configured to keep the first light off while in contact with the surface of the living body.

23. The optical biological information measuring apparatus according to claim 1, wherein said visible light source turns off the first light when the attachment to the living body is detected with said contact detection section.

* * * * *

UNITED STATES PATENT AND TRADEMARK OFFICE
CERTIFICATE OF CORRECTION

PATENT NO. : 8,135,447 B2
APPLICATION NO. : 10/955862
DATED : March 13, 2012
INVENTOR(S) : Kazuya Kondoh et al.

It is certified that error appears in the above-identified patent and that said Letters Patent is hereby corrected as shown below:

On the Title Page: Item [56], References Cited, FOREIGN PATENT DOCUMENTS:
please add the following references:

EP 0898931A     03/1999
WO 03/063704A   08/2003

Signed and Sealed this
Twenty-fourth Day of July, 2012

David J. Kappos
*Director of the United States Patent and Trademark Office*